(12) United States Patent
Liu et al.

(10) Patent No.: US 11,232,558 B2
(45) Date of Patent: Jan. 25, 2022

(54) SYSTEMS AND METHODS FOR IMAGE GENERATION

(71) Applicant: SHANGHAI UNITED IMAGING HEALTHCARE CO., LTD., Shanghai (CN)

(72) Inventors: Hui Liu, Shanghai (CN); Tuoyu Cao, Houston, TX (US); Yuhang Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 38 days.

(21) Appl. No.: 16/568,513

(22) Filed: Sep. 12, 2019

(65) Prior Publication Data
US 2020/0327662 A1 Oct. 15, 2020

(30) Foreign Application Priority Data

Apr. 12, 2019 (CN) .......................... 201910294023.0

(51) Int. Cl.
| | |
|---|---|
| *G06K 9/00* | (2006.01) |
| *G06T 7/00* | (2017.01) |
| *G06T 7/10* | (2017.01) |
| *G16H 30/20* | (2018.01) |
| *G06N 20/00* | (2019.01) |
| *A61B 6/00* | (2006.01) |

(52) U.S. Cl.
CPC .......... *G06T 7/0012* (2013.01); *G06N 20/00* (2019.01); *G06T 7/10* (2017.01); *G16H 30/20* (2018.01); *A61B 6/5229* (2013.01); *G06T 2207/10076* (2013.01); *G06T 2207/10081* (2013.01); *G06T 2207/10088* (2013.01); *G06T 2207/10104* (2013.01)

(58) Field of Classification Search
CPC ..................... G06T 7/0012; G06T 7/10; G06T 2207/10076; G06T 2207/10081; G06T 2207/10088; G06T 2207/10104; G06T 11/00; G06T 11/008; G06T 2211/40; G16H 30/20; G16H 30/40; G16H 50/70; G06N 20/00; A61B 6/5229
See application file for complete search history.

(56) References Cited

U.S. PATENT DOCUMENTS

| | | | |
|---|---|---|---|
| 8,013,307 B2 | 9/2011 | Ye et al. | |
| 2011/0058722 A1 | 3/2011 | Hu et al. | |
| 2017/0061629 A1* | 3/2017 | Zhu | .......................... G06K 9/00 |

(Continued)

OTHER PUBLICATIONS

Osama Mawlaw et al., Truncation Artifact on PET/CT: Impact on Measurements of Activity Concentration and Assessment of a Correction Algorithm, AJR, 186: 1458-1467, 2006.

*Primary Examiner* — Dhaval V Patel
(74) *Attorney, Agent, or Firm* — Metis IP LLC

(57) ABSTRACT

The present disclosure provides a system and method for image generation. The method may include obtaining a first image of a first modality including a complete representation of a subject, obtaining a second image of a second modality including a partial representation of the subject, obtaining a trained machine learning model, generating an synthesized second image including a complete representation of the subject using the trained machine learning model based on the first image and the second image.

20 Claims, 13 Drawing Sheets

(56) References Cited

U.S. PATENT DOCUMENTS

2017/0287113 A1   10/2017  Dwivedi
2019/0340793 A1*  11/2019  Jin .................... G06T 11/005
2020/0311932 A1*  10/2020  Hooper ............... A61B 6/481

* cited by examiner

SYSTEMS AND METHODS FOR IMAGE GENERATION

CROSS-REFERENCE TO RELATED APPLICATIONS

This application claims priority of Chinese Patent Application No. 201910294023.0, filed on Apr. 12, 2019, the contents of which are hereby incorporated by reference.

TECHNICAL FIELD

The disclosure generally relates to imaging systems, and more particularly relates to systems and methods for image generation.

BACKGROUND

Nuclear medicine imaging is widely used in the diagnosis and treatment of various medical conditions based on images acquired by using radiation emission. Positron emission tomography (PET) is an exemplary nuclear medicine imaging technique. PET is used to generate images that may reflect the metabolic activities of a specific organ or tissue (e.g., a tumor). Generally, a PET image was reconstructed from emission data with attenuation correction to present accurate information of a specific organ or tissue in a body. With the development of multi-modality imaging technique (e.g., PET-magnetic resonance (MR) imaging technique), an MR image may be used for attenuation correction of a PET image. However, the radial field of view of an MRI device may be smaller than that of a PET device, which may cause the radial field of view of the MRI device covers only a portion of a subject (e.g., a human body). Therefore, a truncation artifact may present in the MR image obtained by the MRI device, which may result in a quantitative error in the PET image. Therefore, it is desired to provide systems and methods for image generation to reduce the truncation artifact.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a first image of a subject of a first modality. The first image may include a first region and a second region. The first region may include a representation of a first portion of the subject and the second region may include a representation of a second portion of the subject. The system may obtain a second image of the subject of a second modality. The second image may include a third region. The third region may include a representation of the first portion of the subject and the second image may lack a representation of the second portion of the subject. The system may obtain a trained machine learning model. The system may generate a synthesized second image using the trained machine learning model based on the first image and the second image. The synthesized second image may include a fourth region and the third region. The fourth region may include a representation of the second portion of the subject, and the third region may include a representation of the first portion of the subject.

In some embodiments, the first image may include a positron emission tomography (PET) image, the second image may include a magnetic resonance imaging (MRI) image. The system may determine attenuation correction data for the first image based on the synthesized second image. The system may determine a target PET image of the subject based on the attenuation correction data.

In some embodiments, the first image and the second image may be acquired by a same imaging device, and the first image and the second image may be generated using image data acquired by the same imaging device based on different image reconstruction techniques.

In some embodiments, the second image may include a truncation artifact causing the second image to lack a representation of the second portion of the subject.

In some embodiments, the system may obtain multiple groups of training samples. Each group of the multiple groups of training samples may correspond to an object. The system may generate the trained machine learning model by training a machine learning model using the multiple groups of training samples in a training process. For each group of the multiple groups of training samples including a reference image and a pair of a third image and a fourth image of different modalities, the third image and the fourth image may serve as an input of the machine learning model and the reference image may serve as a desired output of the machine learning model during the training process. The third image may include a complete representation of the object, and the fourth image may include a partial representation of the object, and the reference image may include a complete representation of the object corresponding to the fourth image.

In some embodiments, for one of the multiple groups of training samples, the system may obtain an initial third image and an initial fourth image of different modalities of an initial object. The initial third image may include a complete representation of the initial object, and the initial fourth image may include a partial representation of the initial object. The partial representation of the initial object in the initial fourth image may miss a representation of a portion of the initial object. The object may be at least a portion of the initial object less the missing portion of the initial object. The system may determine the reference image based on the initial fourth image. The system may determine the third image based on the initial third image and the reference image. The system may determine the fourth image based on the reference image.

In some embodiments, the system may determine the reference image by decreasing pixel values of pixels in one or more sections of the initial fourth image. The one or more sections may belong to a first specific region of the initial fourth image that corresponds to the initial object less the missing portion. The system may generate the third image by decreasing pixel values of pixels in one or more regions of the initial third image corresponding to the one or more sections of the initial fourth image and a second specific region of the initial fourth image that corresponds to the missing portion.

In some embodiments, the system may designate the initial fourth image as the reference image. The system may generate the third image by decreasing pixel values of pixels in a specific region of the initial third image that corresponds to the missing portion of the initial object not present in the initial fourth image.

In some embodiments, the system may obtain a processed reference image by decreasing pixel values of pixels in one or more regions of the reference image. The system may designate the processed reference image as the fourth image.

In some embodiments, the system may obtain an initial third image of a first modality and an initial fourth image of a second modality of an initial object. The initial third image may include a complete representation of the initial object, the initial fourth image may include a partial representation the initial object. The partial representation of the initial object in the initial fourth image may miss a portion of the initial object. The object may be at least a portion of the initial object less the missing portion of the initial object. The system may obtain a truncated third image by performing a first truncation operation on the initial third image. The truncated third image may include a representation of a portion of the initial object. The system may obtain a truncated fourth image by performing a second truncation operation on the initial fourth image. The truncated fourth image may include a representation of the portion of the initial object present in the truncated third image. The system may designate the truncated third image and the truncated fourth image as the third image and the reference image, respectively. The system may determine the fourth image by performing a third truncation operation on the reference image.

In some embodiments, the trained machine learning model may be constructed based on at least one of a convolutional neural network model (CNN), a fully convolutional neural network (FCN) model, or a generative adversarial network (GAN).

According to a second aspect of the present disclosure, a method is provided. The method may be implemented on at least one computing device, each of which may include at least one processor and a storage device. The method may include obtaining a first image of a subject of a first modality, the first image including a first region and a second region, the first region including a representation of a first portion of the subject, and the second region including a representation of a second portion of the subject. The method may also include obtaining a second image of the subject of a second modality, the second image including a third region, the third region including a representation of the first portion of the subject, and the second image lacking a representation of the second portion of the subject. The method may also include obtaining a trained machine learning model. The method may also include generating a synthesized second image using the trained machine learning model based on the first image and the second image, wherein the synthesized second image includes a fourth region and the third region, the fourth region including a representation of the second portion of the subject, and the third region including a representation includes the first portion of the subject.

According to a third aspect of the present disclosure, a non-transitory computer-readable medium storing at least one set of instructions is provided. When executed by at least one processor, the at least one set of instructions may direct the at least one processor to perform a method. The method may include obtaining a first image of a subject of a first modality, the first image including a first region and a second region, the first region including a representation of a first portion of the subject, and the second region including a representation of a second portion of the subject. The method may also include obtaining a second image of the subject of a second modality, the second image including a third region, the third region including a representation of the first portion of the subject, and the second image lacking a representation of the second portion of the subject. The method may also include obtaining a trained machine learning model. The method may also include generating a synthesized second image using the trained machine learning model based on the first image and the second image, wherein the synthesized second image includes a fourth region and the third region, the fourth region including a representation of the second portion of the subject, and the third region including a representation includes the first portion of the subject.

According to a fourth aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain multiple groups of training samples. Each group of the multiple groups of training samples may correspond to an object. The system may generate a trained machine learning model by training a machine learning model using the multiple groups of training samples. For each group of the multiple groups of training samples including a reference image and a pair of a first image and a second image of different modalities, the first image and the second image may serve as an input of the machine learning model and the reference image may serve as a desired output of the machine learning model during a training process of the machine learning model. The first image may include a complete representation of the object, and the second image may include a partial representation of the object, and the reference image may include a complete representation of the object corresponding to the second image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
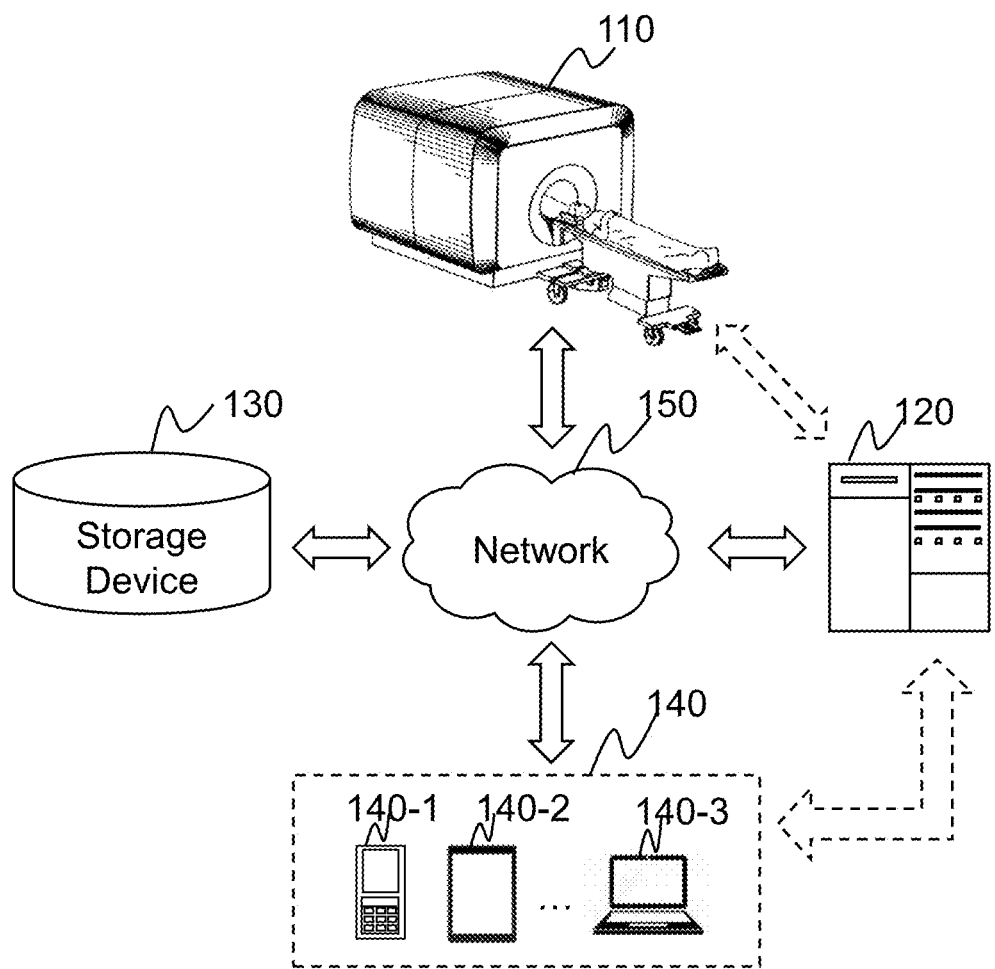
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for image generation. A system may include at least one storage device storing executable instructions, and at least one processor in communication with the at least one storage device. When executing the executable instructions, the at least one processor may cause the system to obtain a first image of a subject acquired by the first imaging device of a first modality. The first image may include a first region and a second region. The first region may include a representation of a first portion of the subject and the second region may include a representation of a second portion of the subject. The at least one processor may also cause the system to obtain a second image of the subject acquired by a second imaging device of a second modality. The second image may include a third region. The third region may include a representation of the first portion of the subject and the second image may lack a representation of the second portion of the subject. The at least one processor may further cause the system to obtain a trained machine learning model, and generate a synthesized second image using the trained machine learning model based on the second region in the first image and a degree of similarity between the first region and the third region. The synthesized second image may include a fourth region. The fourth region may include a representation of the second portion of the subject.

Accordingly, the system may input two images of different modalities, one of a first modality including a complete representation of a subject and one of a second modality including a partial representation of the subject, into the trained machine learning model. The system may generate a synthesized image (also referred to as an extended second image) of the second modality including a complete representation of the subject. The synthesized image corresponding to the image of the second modality that includes the partial representation of the subject may be generated by directly using the trained machine learning model, which may improve the processing speed for generating the synthesized image. The systems and methods of embodiments of the present disclosure may be conveniently applied in different clinical situations. In some embodiments, the image of the first modality may be a PET image of a subject, and the image of the second modality may be an MR image of the subject. The system may determine attenuation correction data for the PET image based on the synthesized MR image, and determine a target PET image of the subject based on the attenuation correction data. Accordingly, the system may improve the efficiency and accuracy of attenuation correction of a PET image by a corresponding MR image.

FIG. 1 is a schematic diagram illustrating an exemplary imaging system 100 according to some embodiments of the present disclosure. In some embodiments, the imaging system 100 may be a single-modality system or a multi-modality system. Exemplary single-modality systems may include a positron emission tomography (PET) system, a magnetic resonance (MR) system, etc. Exemplary multi-modality systems may include a magnetic resonance-positron emission tomography (MR-PET) system, etc. In some embodiments, the imaging system 100 may include modules and/or components for performing imaging and/or related analysis.

Merely by way of example, as illustrated in FIG. 1, the imaging system 100 may include a medical device 110, a processing device 120, a storage device 130, one or more terminals 140, and a network 150. The components in the imaging system 100 may be connected in one or more of various ways. Merely by way of example, the medical device 110 may be connected to the processing device 120 through the network 150. As another example, the medical device 110 may be connected to the processing device 120 directly as illustrated in FIG. 1. As a further example, the terminal(s) 140 may be connected to another component of the imaging system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The medical device 110 may be configured to acquire imaging data relating to at least one part of a subject. The imaging data relating to at least one part of a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof.

In some embodiments, the medical device 110 may include a single modality imaging device. For example, the medical device 110 may include a positron emission tomography (PET) device, a single-photon emission computed tomography (SPECT) device, a magnetic resonance imaging (MRI) device (also referred to as an MR device, an MR scanner), a computed tomography (CT) device, or the like, or any combination thereof. In some embodiments, the medical device 110 may include a multi-modality imaging device. Exemplary multi-modality imaging devices may include a PET-CT device, a PET-MRI device, or the like, or a combination thereof. For example, the medical device 110 may include a PET device and an MRI device. The PET device may scan a subject or a portion thereof that is located within its detection region and generate projection data relating to the subject or the portion thereof. The PET device may include a gantry, a detector, an electronics module, and/or other components not shown. The gantry may support one or more parts of the PET device, for example, the detector, the electronics module, and/or other components. The detector may detect radiation photons (e.g., γ photons) emitted from a subject being examined. The electronics module may collect and/or process electrical signals (e.g., scintillation pulses) generated by the detector. The electronics module may convert an analog signal (e.g., an electrical signal generated by the detector) relating to a radiation photon detected by the detector to a digital signal relating to a radiation event. As used herein, a radiation event (also referred to as a single event) may refer to an interaction between a radiation photon emitted from a subject and impinging on and detected by the detector. A pair of radiation photons (e.g., γ photons) interacting with two detector blocks along a line of response (LOR) within a coincidence time window may be determined as a coincidence event. A portion of the radiation photons (e.g., γ photons) emitted from a subject being examined may interact with tissue in the subject. The radiation photons (e.g., γ photons) interacting with tissue in the subject may be scattered or otherwise change its trajectory, that may affect the number or count of radiation photons (e.g., γ photons) detected by two detector blocks along a line of response (LOR) within a coincidence time window and the number or count of coincidence events.

The MRI device may scan a subject or a portion thereof that is located within its detection region and generate MR image data relating to the subject or the portion thereof. The MR image data may include k-space data, MR signals, an MR image, etc. The MR image data may be acquired by the MRI device via scanning the subject using a pulse sequence. Exemplary pulse sequences may include a spin-echo sequence, a gradient echo sequence, a diffusion sequence, an inversion recovery sequence, or the like, or any combination thereof. For example, the spin-echo sequence may include a fast spin-echo (FSE), a turbo spin-echo (TSE), a rapid acquisition with relaxation enhancement (RARE), a half-Fourier acquisition single-shot turbo spin-echo (HASTE), a turbo gradient spin echo (TGSE), or the like, or a combination thereof.

The processing device 120 may process data and/or information obtained from the medical device 110, the terminal(s) 140, and/or the storage device 130. For example, the processing device 120 may obtain a first image of a subject acquired by a first imaging device of a first modality. The processing device 120 may also obtain a second image of the subject acquired by a second imaging device of a second modality. The processing device 120 may further obtain a trained machine learning model. The processing device 120 may generate a synthesized second image using the trained machine learning model based on the second region in the first image and a degree of similarity between the first region and the third region. As another example, the processing device 120 may determine attenuation correction data for the first image based on the synthesized second image. The processing device 120 may determine a target image of the subject based on the attenuation correction data. As still another example, the processing device 120 may obtain multiple groups of training samples. The processing device 120 may generate the trained machine learning model by training a machine learning model using the multiple groups of training samples. As a further example, the processing device 120 may obtain an initial third image of a first modality and an initial fourth image of a second modality of an initial object. The processing device 120 may determine a reference image based on a specific region of the initial fourth image. The processing device 120 may determine a third image based on the initial third image and the reference image. The processing device 120 may determine a fourth image based on the reference image and the initial fourth image. The processing device 120 may determine the third image, the fourth image and the reference image as a group of training samples. The trained machine learning model may be updated from time to time, e.g., periodically or not, based on a sample set that is at least partially different from the original sample set from which the original trained machine learning model is determined. For instance, the trained machine learning model may be updated based on a sample set including new samples that are not in the original sample set, samples processed using the machine learning model in connection with the original trained machine learning model of a prior version, or the like, or a combination thereof. In some embodiments, the determination and/or updating of the trained machine learning model may be performed on a processing device, while the application of the trained machine learning model may be performed on a different processing device. In some embodiments, the determination and/or updating of the trained machine learning model may be performed on a processing device of a system different than the imaging system 100 or a server different than a server including the processing device 120 on which the application of the trained machine learning model is performed. For instance, the determination and/or updating of the trained machine learning model may be performed on a first system of a vendor who provides and/or maintains such a machine learning model and/or has access to training samples used to determine and/or update the trained machine learning model, while image generation based on the provided machine learning model may be performed on a second system of a client of the vendor. In some embodiments, the determination and/or updating of the trained machine learning model may be performed online in response to a request for image generation. In some embodiments, the determination and/or updating of the trained machine learning model may be performed offline.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include image data acquired by the processing device 120, algorithms and/or models for processing the image data, etc. For example, the storage device 130 may store image data (e.g., PET images, MR images, PET projection data, etc.) acquired by the medical device 110. As another example, the storage device 130 may store one or more algorithms for processing the image data, a trained machine learning model for image generation, etc. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the medical device 110 (e.g., an MRI device, a PET device, etc.), the terminal(s) 140, the processing device 120, the storage device 130, etc., may communicate information and/or data with one or more other components of the imaging system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios.

Figure 2:
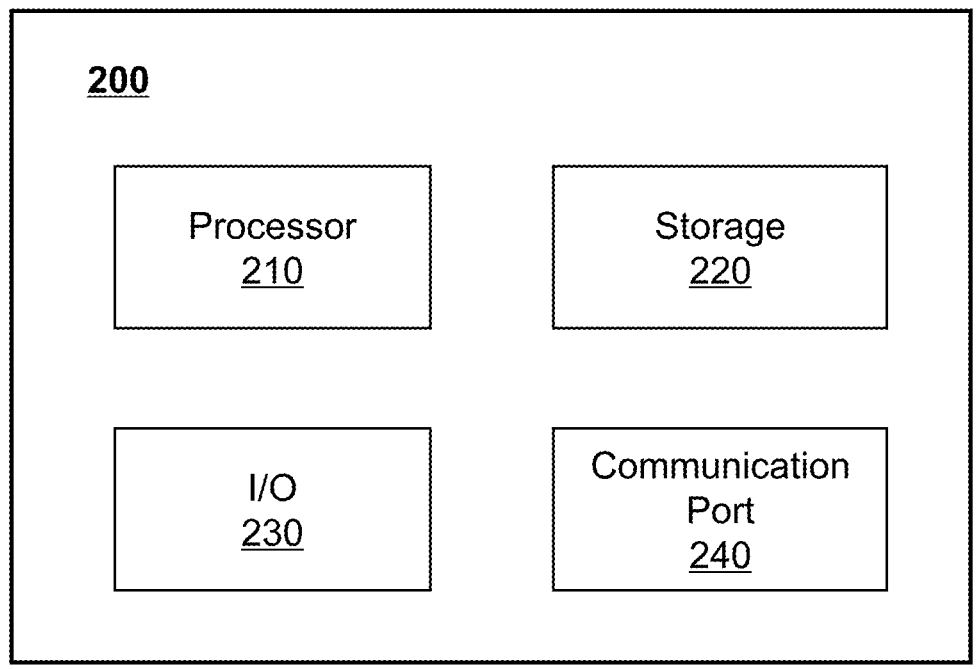
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the medical device 110, the terminal(s) 140, the storage device 130, and/or any other component of the imaging system 100. Specifically, the processor 210 may process one or more measured data sets obtained from the medical device 110. For example, the processor 210 may generate an image based on the data set(s). In some embodiments, the generated image may be stored in the storage device 130, the storage 220, etc. In some embodiments, the generated image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for generating attenuation correction data for a PET image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
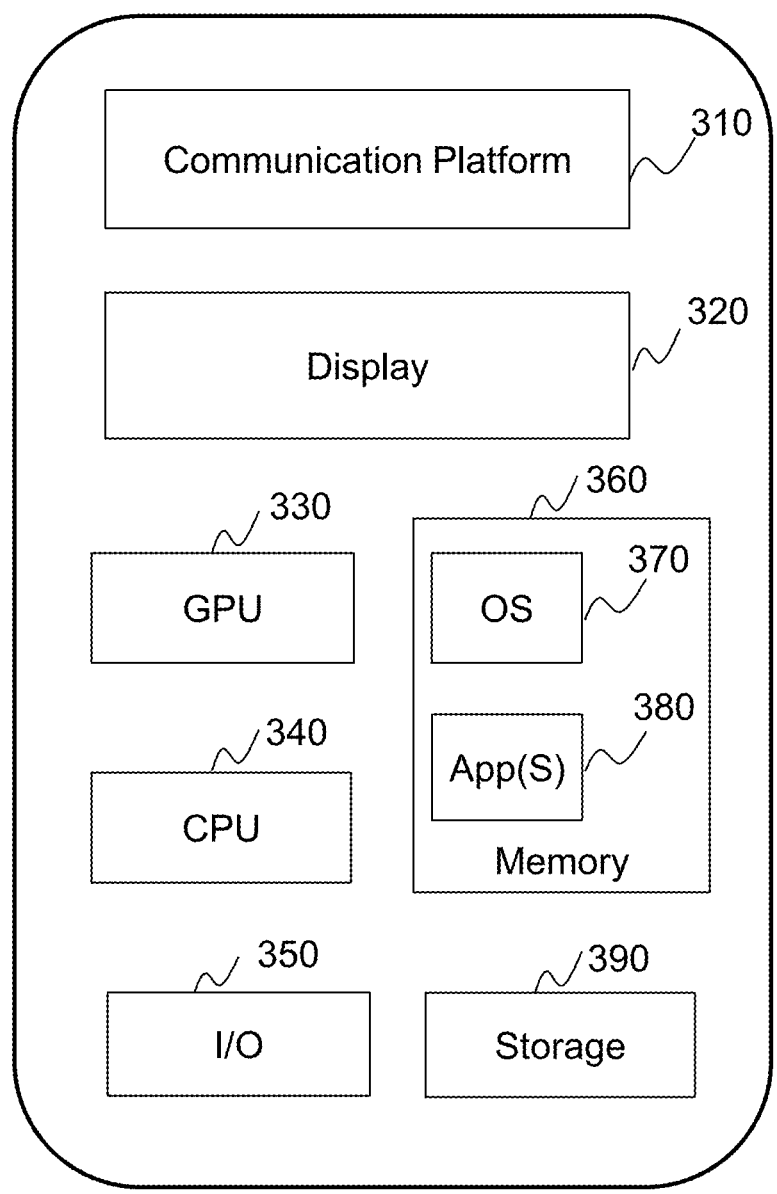
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
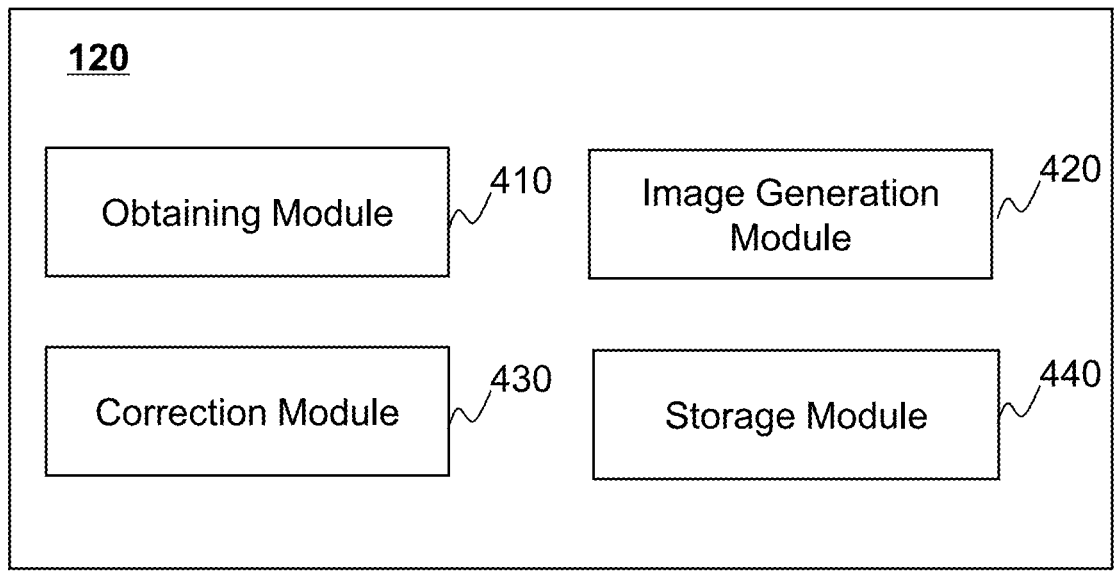
FIG. 4A is a block diagram illustrating an exemplary processing device according to some embodiments of the present disclosure.

FIG. 4A is a block diagram illustrating exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4A, the processing device 120 may include an obtaining module 410, an image generation module 420, a correction module 430, and a storage module 440. Each of the modules described above may be a hardware circuit that is designed to perform certain actions, e.g., according to a set of instructions stored in one or more storage media, and/or any combination of the hardware circuit and the one or more storage media.

The obtaining module 410 may be configured to obtain one or more images. In some embodiments, the obtaining module 410 may obtain a first image of a subject acquired by a first imaging device of a first modality. As used herein, a modality associated with a specific image (e.g., the first image) of a specific subject may be defined by an imaging device acquiring the specific image, one or more scanning parameters used by the imaging device scanning the specific subject, an image reconstruction technique for generating the specific image, or the like, or any combination thereof. In some embodiments, the first image may include a complete representation of the subject. The first image may include a first region including a representation of a first portion of the subject and a second region including a representation of a second portion of the subject. The obtaining module 410 may also be configured to obtain a second image of the subject acquired by a second imaging device of a second modality. The second modality may be different from the first modality. The second image may include a partial representation of the subject with respect to the first image. The second image may include a third region including a representation of the first portion of the subject and a fourth region lacking a representation of the second portion of the subject. In some embodiments, the obtaining module 410 may obtain the first image and/or the second image from the first imaging device and/or the second imaging device (e.g., the medical device 110), the processing device 120, the storage device 130, or any other storage device. The obtaining module 410 may also be configured to obtain a trained machine learning model. The trained machine learning model may be configured to generate a synthesized image including a complete representation of a specific subject based on a specific image (e.g., a truncated image including a truncation artifact, the second image, etc.) lacking a representation of a portion of the specific subject.

The image generation module 420 may be configured to generate a synthesized second image using the trained machine learning model based on the first image and the second image. The synthesized second image may include a complete representation of the subject corresponding to the second image. In some embodiments, the image generation module 420 may input the first image and the second image into the trained machine learning model to determine the synthesized second image. In some embodiments, the image generation module 420 may generate the synthesized second image based on the second region of the first image and the similarity degree between the first region of the first image and the third region of the second image.

In some embodiments, the first image may be a PET image acquired by a PET device and the second image may be an MR image acquired by an MRI device. The image generation module 420 may determine a synthesized MR image according to the PET image and the MR image using the trained machine learning model. The image generation module 420 may also be configured to determine a target PET image of the subject based on attenuation correction data determined by the correction module 430 as described below.

The correction module 430 may be configured to determine attenuation correction data for the PET image (i.e., the first image) based on the synthesized MR image. In some embodiments, the correction module 430 may determine attenuation correction data for the PET image (i.e., the first image) based on the synthesized MR image using a segmentation technique. Specifically, an object represented in the synthesized MR image and/or the PET image may be identified and classified into different portions (e.g., water, adipose tissues, bone tissues, lungs, etc.). The various portions represented in the PET image and the synthesized MR image may be fused and assigned various attenuation coefficients (or values) according to clinical experience. The attenuation correction data associated with the PET image may be determined based on the various attenuation coefficients (or values) corresponding to various portions (e.g., water, adipose tissue, bone tissue, lungs, etc.) of the subject. In some embodiments, the attenuation correction data associated with the PET image may be generated using a body map technique based on the synthesized MR image. Using the body map technique, the synthesized MR image may be registered with a reference body map including various attenuation coefficients (or values) corresponding to different tissues or organs. The attenuation correction data associated with the PET image may be generated based on the registration.

The storage module 440 may be configured to store data and/or instructions associated with the imaging system 100. For example, the storage module 440 may store data of the first image acquired by the first imaging device, the second image acquired by the second imaging device, the trained machine learning model, and/or one or more correction techniques (e.g., a segmentation technique, a body map technique, etc.), one or more image reconstruction techniques, etc. In some embodiments, the storage module 440 may be the same as the storage device 130 and/or the storage module 480 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the image generation module 420 and the correction module 430 may be integrated into a single module. As another example, some other components/modules may be added into the processing device 120.

Figure 4B:
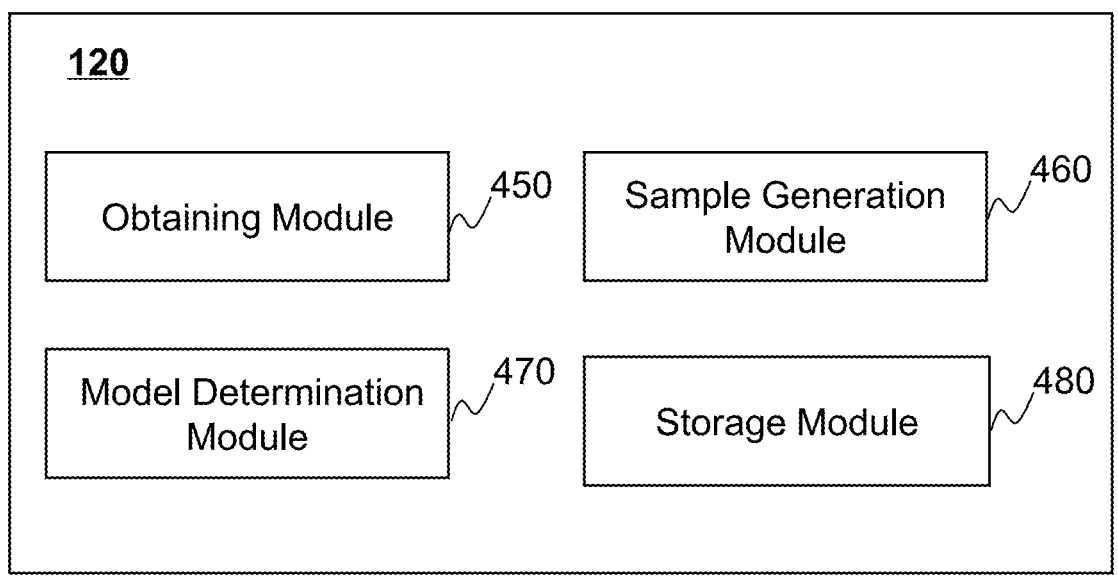
FIG. 4B is a block diagram illustrating an exemplary processing device according to some embodiments of the present disclosure.

FIG. 4B is a block diagram illustrating exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4B, the processing device 120 may include an obtaining module 450, a sample generation module 460, a model determination module 470, a storage module 480. Each of the modules described above may be a hardware circuit that is designed to perform certain actions, e.g., according to a set of instructions stored in one or more storage media, and/or any combination of the hardware circuit and the one or more storage media.

The obtaining module 450 may be configured to obtain an initial third image and an initial fourth image of an initial object of different modalities. The initial third image may include a complete representation of the initial object. The initial third image may include one or more regions. Each of the one or more regions may include a representation of a portion of the initial object. In some embodiments, the initial fourth image may include a complete representation of the initial object. In some embodiments, the initial fourth image may include a partial representation of the initial object. The initial fourth image may lack a representation of a portion of the initial object. The portion of the initial object not represented in the initial fourth image may be also referred to as a first missing portion of the initial object. The obtaining module 450 may obtain the initial third image and the initial fourth image by an imaging device via scanning the initial object.

The sample generation module 460 may be configured to determine a training sample including a reference image and a pair of a third image and a fourth image of different modalities. The training sample may correspond to an object. The object may be at least a portion of the initial object. The third image may include a complete representation of the object and the fourth image may include a partial representation of the object. The reference image may correspond to the fourth image and include a complete representation of the object with respect to the fourth image.

In some embodiments, the sample generation module 460 may designate the reference image as the initial fourth image. If the reference image includes a complete representation of the initial object with respect to the initial third image, the sample generation module 460 may designate the initial third image as the third image. If the reference image includes a partial representation of the initial object with respect to the initial third image, the sample generation module 460 may determine the third image by removing a representation of the first missing portion of the initial object from the initial third image. In some embodiments, the sample generation module 460 may determine the reference image by removing a portion of a representation of the initial object from the initial fourth image. The object represented in the reference image may include the initial object less a second missing portion. If the initial fourth image includes a partial representation of the initial object, the second missing portion of the initial object may include the first missing portion of the initial object. If the initial fourth image includes a complete representation of the initial object, the second missing portion of the initial object may be any portion of the initial object. The sample generation module 460 may determine the third image by removing a representation of the second missing portion of the initial object from the initial third image. The sample generation module 460 may determine the fourth image based on the reference image and the initial fourth image. For example, the sample generation module 460 may generate the fourth image by removing a representation of a portion of the object from the reference image.

In some embodiments, a truncated third image may be obtained by performing a first truncation operation on the initial third image. The truncated third image may include a representation of a portion of the initial object. A truncated fourth image may be obtained by performing a second truncation operation on the initial fourth image. The truncated fourth image may include a representation of the portion of the initial object represented in the truncated third image. The sample generation module 460 may designate the truncated third image and the truncated fourth image as the third image and the reference image, respectively. The fourth image may be obtained by performing a third truncation operation on the reference image.

The model determination module 470 may be configured to generate a trained machine learning model by training a machine learning model using the multiple groups of training samples in a training process. In some embodiments, the model determination module 470 may construct the trained machine learning model based on a convolutional neural network model (CNN), a fully convolutional neural network (FCN) model, a generative adversarial network (GAN) model, or the like, or any combination thereof. The model determination module 470 may train the machine learning model based on the multiple groups of training samples using a training algorithm. In some embodiments, the model determination module 470 may perform a plurality of iterations to iteratively update one or more parameter values of the machine learning model to obtain the trained machine learning model. Before the plurality of iterations, the model determination module 470 may initialize the parameter values of the machine learning model.

The storage module 480 may be configured to store data and/or instructions associated with the imaging system 100. For example, the storage module 480 may store data of multiple groups of training samples, initial third images, initial fourth images, one or more machine learning models, a trained machine learning model, etc. In some embodiments, the storage module 480 may be same as the storage device 130 and/or the storage module 440 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the obtaining module 450 and the sample generation module 460 may be integrated into a single module. As another example, some other components/modules may be added into the processing device 120.

Figure 5:
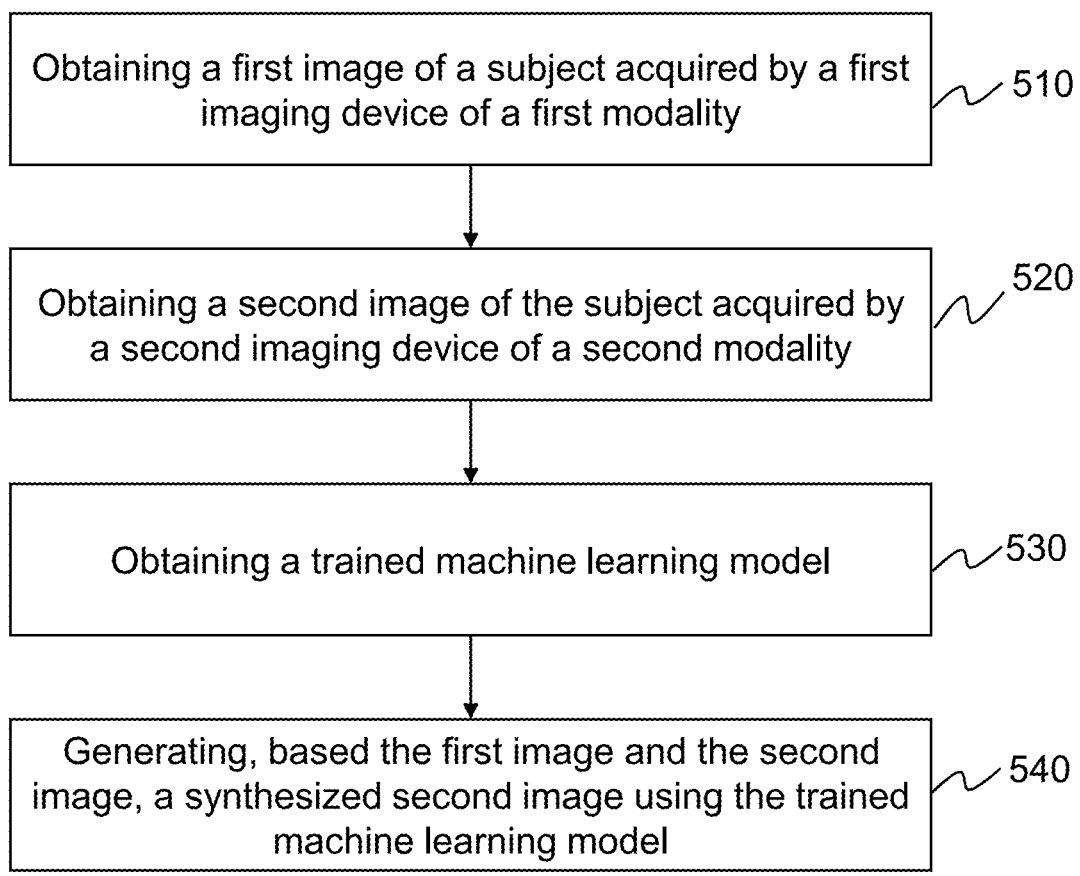
FIG. 5 is a schematic flowchart illustrating an exemplary process for generating an image of a subject according to some embodiments of the present disclosure.

FIG. 5 is a schematic flowchart illustrating an exemplary process for generating an image of a subject according to some embodiments of the present disclosure. In some embodiments, process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 510, the processing device 120 (e.g., the obtaining module 410) may obtain a first image of a subject acquired by a first imaging device of a first modality. The subject may be biological or non-biological. For example, the subject may include a patient, a man-made object, etc. as described elsewhere in the present disclosure (e.g., FIG. 1 and the descriptions thereof). In some embodiments, the first image may be obtained from the first imaging device (e.g., the medical device 110), the processing device 120, the storage device 130, or any other storage device. For example, the first imaging device may transmit acquired first imaging data (e.g., projection data) to the storage device 130, the storage module 440, or any other storage device for storage. The processing device 120 may obtain the first imaging data from the storage device 130, the storage module 440, or any other storage device and generate the first image based on the first imaging data. As another example, the processing device 120 may obtain the first image from the first imaging device directly.

As used herein, a modality of a specific image (e.g., the first image) of a specific subject may be defined by an imaging device acquiring the specific image, one or more scanning parameters used by the imaging device scanning the specific subject, an image reconstruction technique for generating the specific image, or the like, or any combination thereof. Different images of a same subject acquired by different imaging devices may correspond to different modalities. For example, an MR image of a specific subject obtained by an MRI device may be considered of a different modality than a PET image of the specific subject obtained by a PET device. Different images of a same subject generated using different image reconstruction techniques based on same imaging data (e.g., projection data) may correspond to different modalities. For example, an image generated using an image reconstruction technique (e.g., a back-projection technique) based on imaging data (e.g., projection data) may be considered of a different modality than another image generated using another image reconstruction technique (e.g., an iteration reconstruction technique) based on the same imaging data (e.g., projection data). As another example, an MR image reconstructed using a T1 weighted imaging technique may be considered of a different modality than another MR image generated using a T2 weighted imaging technique based on same MR signals (i.e., echo signals). Different images generated using a same imaging device but based on different scanning parameters may correspond to different modalities. For example, an MR image generated based on k-space data acquired by an MRI device according to a spin-echo sequence may be considered of a different modality than another MR image generated based on k-space data acquired by the same MRI device according to a gradient echo sequence. As another example, MR images generated based on a gradient echo sequence with partially and entirely different scanning parameters, respectively, may be considered of different modalities.

In some embodiments, the first image of the first modality may be generated based on the first imaging data (e.g., projection data) acquired by the first imaging device via scanning the subject according to one or more first scanning parameters. For example, the first image of the first modality may be reconstructed based on the first imaging data using a first image reconstruction technique. The first imaging device may include a PET device, a SPECT device, an MRI device, a CT device, or the like, or any combination thereof. For an MR scanning, the first scanning parameters may include parameters relating to an RF pulse (e.g., the number (or count) of excitations (NEX), a bandwidth, etc.) emitted by an RF coil, parameters relating to gradient fields generated by gradient coils, parameters relating to MR signals (e.g., an echo time (TE), an echo train length (ETL), a spin echo type, the number (or count) of phases), image contrast, a slice thickness, T1, T2, an acquisition time (TA), or the like, or any combination thereof. For a PET scanning, the first scanning parameters may include parameters relating to a field of view, a sampling frequency, a scanning bed feed speed, a window width, a scanning time, a scanning speed, or the like, or any combination thereof. For a CT scanning, the first scanning parameters may include parameters relating to a scanning type (e.g., a plain scan, a spiral scan), a tube voltage, a tube current, a scanning time, a field of view, a slice thickness, a rotation speed of a gantry, or the like, or any combination thereof. The first image reconstruction technique may include a Fourier transform (FT), an iterative reconstruction, a backward projection (e.g., a convolution back-projection technique, a filtered back-projection technique), or the like, or any combination thereof.

In some embodiments, the first image may include a complete representation of the subject using a plurality of pixels or voxels with pixel/voxel values or characteristics, e.g., luminance values, gray values, colors (or RGB values), saturation values, etc. The first image may include one or more regions. Each of the one or more regions may include a representation of a portion of the subject. For example, the subject represented in the first image may include a first portion and a second portion. The first image may include a first region and a second region. The first region may include a representation of the first portion of the subject. The second region may include a representation of the second portion of the subject. As used herein, an image including a complete representation of a specific subject may refer to that each portion or position of the specific subject may be represented in the image using one or more pixels or voxels with pixel/voxel values or characteristics. An image including a partial representation of a specific subject may refer to that a portion or position of the specific subject may correspond to one or more pixels or voxels in the image without pixel/voxel values or characteristics, i.e., the image may lack a representation of the portion or position of the specific subject. Signal or information (e.g., imaging data) corresponding to a portion or position of the specific subject that is not represented in the image may be missing, removed, overwritten, or otherwise not presented in the image. For instance, the region lacking representation of the portion or position of the specific subject may be black in the image. Pixel (or voxel) values of pixels (or voxels) in the region of the image that corresponds to the portion or position of the specific subject not represented in the image may be set to 0. The portion or position of the specific subject corresponding to one or more pixels or voxels without characteristics may be also referred to as a missing portion of the specific subject not represented in the image.

In 520, the processing device 120 (e.g., the obtaining module 410) may obtain a second image of the subject acquired by a second imaging device of a second modality. In some embodiments, the second image may be obtained from the second imaging device (e.g., the medical device 110), the processing device 120, the storage device 130, or any other storage device. For example, the second imaging device may transmit acquired second imaging data to the storage device 130, the storage module 440, or any other storage device for storage. The processing device 120 may obtain the second imaging data from the storage device 130, the storage module 440, or any other storage device and generate the second image based on the second imaging data. As another example, the processing device 120 may obtain the second image from the second imaging device directly.

In some embodiments, the second image of the second modality may be generated based on the second imaging data (e.g., k-space data) acquired by the second imaging device via scanning the subject according to one or more second scanning parameters. For example, the second image of the second modality may be reconstructed based on the second imaging data using a second image reconstruction technique. The second imaging device may include a PET device, a SPECT device, an MRI device, a CT device, or the like, or any combination thereof. The second image reconstruction technique may include a Fourier transform (FT), an iterative reconstruction, a backward projection (e.g., a convolution back-projection technique, a filtered back-projection technique), or the like, or any combination thereof.

The second imaging device may be the same as or different from the first imaging device. For example, the first imaging device may be a PET device and the second imaging device may be an MRI device. As another example, the first imaging and the second imaging device may be the same (one single) MRI device. The second image reconstruction technique may be different from or the same as the first image reconstruction technique. For example, the first image and the second image may be reconstructed both using the same iterative reconstruction technique. The second scanning parameters may be partially different (one or more scanning parameters being the same as and one or more other scanning parameters being different) or entirely different (all scanning parameters being different) from the first scanning parameters or the same as the first scanning parameters.

The second modality may be different from the first modality. In some embodiments, the first image and the second image may be reconstructed based on same imaging data (e.g., same k-space data), while the first image reconstruction technique on the basis of which the first image is generated and the second image reconstruction technique on the basis of which the first image is generated may be different. For example, the first image reconstruction technique may include a T1 weighted imaging technique and the second image reconstruction technique may include a T2 weighted imaging technique. In some embodiments, the first image and the second image may be acquired, respectively, by the first imaging device and the second imaging device which are two different imaging devices. For example, the first imaging device may include a PET device and the second imaging device may include an MRI device. In some embodiments, the first imaging device and the second imaging device may be the same imaging device (e.g., the same MRI device), and the first scanning parameters and the second scanning parameters may be at least partially different. For example, if the first imaging device and the second imaging device is the same MRI device, the first image and the second image may be acquired based on different pulse sequences. As a further example, the first image may be acquired based on a spin-echo sequence and the second image may be acquired based on a gradient echo sequence. As still a further example, the first image and the second image may be acquired based on different gradient echo sequences with at least partially different scanning parameter values, such as different echo times, different repetition times, etc.

Figure 9:
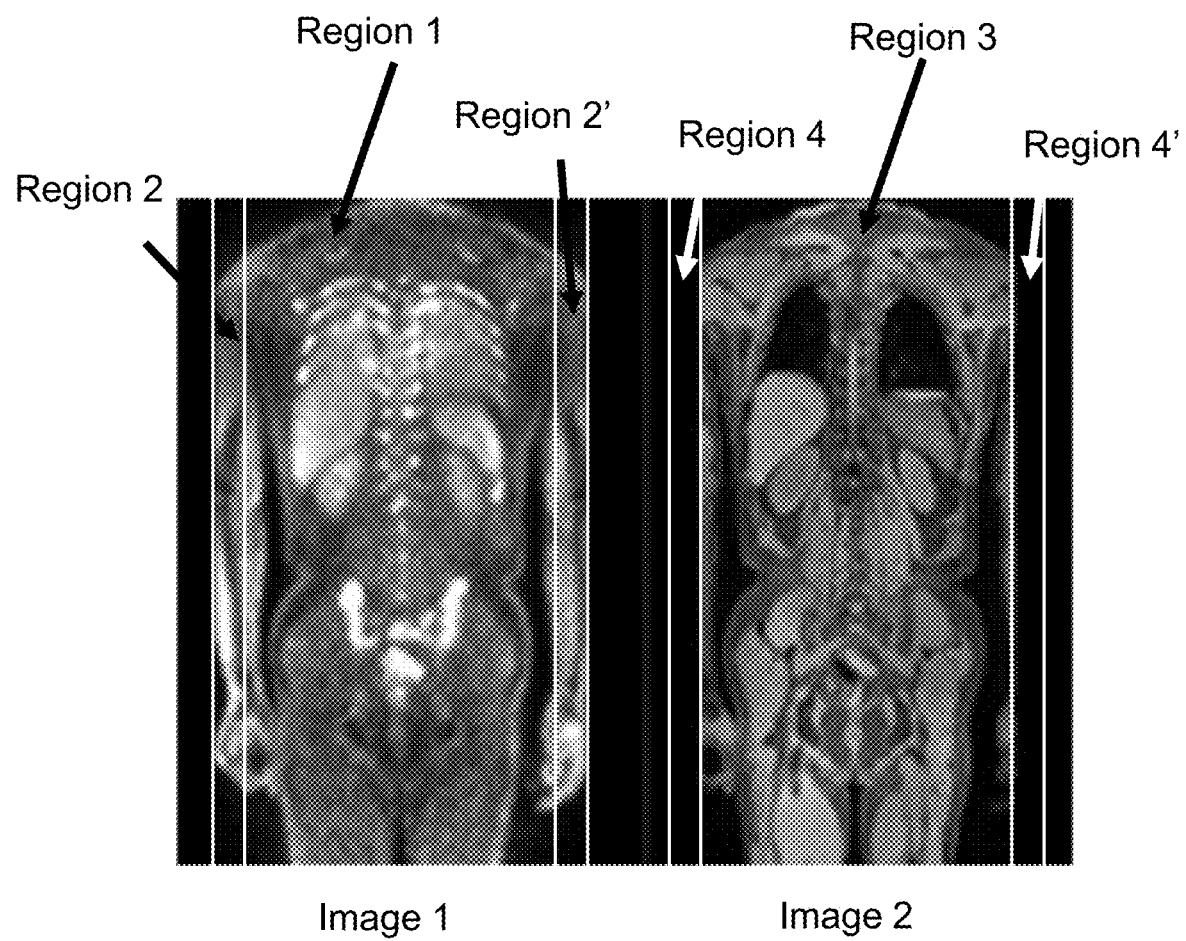
FIG. 9 shows exemplary images of different modalities according to some embodiments of the present disclosure.

The second image may include a partial representation of the subject with respect to the first image. In other words, the second image may lack a representation of a portion of the subject. The portion of the subject not represented in the second image may be also referred to as a missing portion of the subject. For example, the second image may include a third region and a fourth region. The third region may include a representation of the first portion of the subject. The second image or the fourth region may lack a representation of the second portion of the subject. The second portion of the subject may be also referred to as a missing portion of the subject. In some embodiments, the lacking of the representation of the portion of the subject in the second image may be caused by a truncation artifact, a metal artifact, etc. Merely for illustration, as shown in FIG. 9, image 2 includes region 3 and regions 4 and 4'. Regions 4 and 4' lack representations of a portion of the arms of a subject with respect to regions 2 and 2' including representations of the portion of the arms of the subject. Region 4 and 4' are black in image 2.

In some embodiments, sizes of the first image and the second image may be different. The processing device 120 may perform an interpolation operation on the first image and/or the second image such that the sizes of the first image and the second image may be same. In some embodiments, the sizes of the first image and the second image may be same. As used herein, a size of an image may refer to a count or number of pixels or voxels in the image. Each of pixels or voxels in the first image (or the interpolated first image) may correspond to one of pixels or voxels in the second image (or the interpolated first image). As used herein, two corresponding pixels (or voxels) in the first image and the second image may correspond to a same physical portion or position of the subject. For example, the first image may include a plurality of first pixels or voxels corresponding to different portions or positions of the subject. The second image may include a plurality of second pixels or voxels corresponding to different portions or positions of the subject. Each of the plurality of first pixels or voxels may correspond to one of the plurality of second pixels or voxels. Characteristics of first pixels or voxels in the first region of the first image may be similar to characteristics of second pixels or voxels in the third region of the second image as the first region of the first image and the third region of the second image correspond to the first portion of the subject. In other words, a similarity degree between characteristics of first pixels or voxels in the first region of the first image and characteristics of second pixels or voxels in the third region of the second image (i.e., a level of similarity between the first region and the third region) may exceed a threshold. Characteristics of first pixels or voxels in the second region of the first image may be similar to characteristics of second pixels or voxels in the fourth region of the second image if the fourth region includes a representation of the second portion of the subject. Accordingly, process 500 may generate an synthesized second image including the representation of the second portion of the subject as described in operations 530 and 540 using a trained machine learning model based on the similarity degree between characteristics of first pixels or voxels in the first region of the first image and characteristics of second pixels or voxels in the third region of the second image and the second region of the first image.

In 530, the processing device 120 (e.g., the obtaining module 410) may obtain a trained machine learning model. The trained machine learning model may be configured to generate a synthesized image (also referred to as an extended image) including a complete representation of a specific subject based on a specific image (e.g., a truncated image including a truncation artifact, the second image, etc.) lacking a representation of a portion of the specific subject. The trained machine learning model may generate a synthesized image based on the specific image and a reference image including a complete representation of the specific subject (e.g., the first image referred to in 540). The reference image and the specific image may be of different modalities. In some embodiments, the trained machine learning model may be configured to provide a mapping relationship between the specific image lacking the representation of the portion of the specific subject and the synthesized image including the complete representation of the specific subject. The trained machine learning model may be configured to generate the synthesized image according to the mapping relationship. The mapping relationship between the specific image lacking the representation of the portion of the specific subject and the synthesized image including the complete representation of the specific subject may reflect a similarity degree between the synthesized image including the complete representation of the specific subject and the reference image including the complete representation of the specific subject.

In some embodiments, the trained machine learning model may divide the reference image and the synthesized image into one or more regions (also referred to as small regions). Each small region in the reference image may correspond to one small region in the synthesized image. The trained machine learning model may extract one or more features for each small region from the reference image and/or the synthesized image. In some embodiments, the one or more features of each small region may include color information, edge information, texture information, shape information, or the like, or any combination thereof. Exemplary color information may include values associated with RGB, HSV, YUV, YIQ, etc. Exemplary edge information may include high-frequency component information, edge histogram information, etc. Exemplary texture information may include information associated with a homogeneous texture, a texture browsing, etc. Exemplary shape information may include information associated with a region shape, a contour shape, a shape 3D, etc. The trained machine learning model may determine a weight for each small region based on the extracted one or more features. For example, if a representative value of a feature of a specific small region is 255, a weight of 0.5 may be determined for the specific small region. If a representative value of the feature of another specific small region is 220, a weight of 0.4 may be determined for the another specific small region. The trained machine learning model may determine a small region similarity between a small region in the reference image and the corresponding small region in the synthesized image based on the weights. For example, if a weight of small region in the reference image is 0.5, a weight of a corresponding small region in the synthesized image is 0.4, the trained machine learning model may determine a small region similarity between the small region in the reference image and the corresponding small region in the synthesized image as 20%. The trained machine learning model may determine a similarity between the synthesized image and the reference image based on one or more weight of the one or more small regions. For example, the trained machine learning model may determine an average value of the one or more small region similarities as the similarity between the synthesized image and the reference image.

In some embodiments, the processing device 120 may retrieve the trained machine learning model from the storage device 130, the terminals(s) 140, or any other storage device. For example, the trained machine learning model may be obtained by training a machine learning model offline using a processing device different from or same as the processing device 120. The trained machine learning model may be stored in the storage device 130, the terminals(s) 140, or any other storage device. The processing device 120 may retrieve the trained machine learning model from the storage device 130, the terminals(s) 140, or any other storage device in response to receipt of a request for image generation. More descriptions regarding the training of the machine learning model for anomaly detection may be found elsewhere in the present disclosure. See, e.g., FIG. 6, and relevant descriptions thereof.

In 540, the processing device 120 (e.g., the image generation module 420) may generate a synthesized second image (also referred to as an extended second image) using the trained machine learning model based on the first image and the second image. The synthesized second image may include a fourth region including a representation of the second portion of the subject. The synthesized second image may include a complete representation of the subject corresponding to the second image. In some embodiments, the processing device 120 may input the first image and the second image into the trained machine learning model to determine the synthesized second image. In some embodiments, the processing device 120 may transmit the synthesized second image to a terminal (e.g., the terminal(s) 140 in the imaging system 100).

In some embodiments, the processing device 120 may generate the synthesized second image based on the second region of the first image and the similarity degree between the first region of the first image and the third region of the second image. For example, the processing device 120 may generate the synthesized second image using the trained machine learning model such that the similarity degree between the second region of the first image and the fourth region of the synthesized second image is close to or same as the similarity degree between the first region of the first image and the third region of the synthesized second image.

In some embodiments, the first image may be a PET image acquired by a PET device and the second image may be an MR image acquired by an MRI device. The processing device 120 may determine a synthesized MR image according to the PET image and the MR image using the trained machine learning model. The processing device 120 (e.g., the correction module 430) may determine attenuation correction data for the PET image (i.e., the first image) based on the synthesized MR image. For example, the processing device 120 may determine attenuation correction data for the PET image (i.e., the first image) based on the synthesized MR image using a segmentation technique. Specifically, an object represented in the synthesized MR image and/or the PET image may be identified and classified into different portions (e.g., water, adipose tissues, bone tissues, lungs, etc.). The various portions represented in the PET image and the synthesized MR image may be fused and assigned various attenuation coefficients (or values) according to information from, e.g., clinical experience. The attenuation correction data associated with the PET image may be determined based on the various attenuation coefficients (or values) corresponding to various portions (e.g., water, adipose tissue, bone tissue, lungs, etc.) of the subject. As another example, the attenuation correction data associated with the PET image may be generated using a body map technique based on the synthesized MR image. Using the body map technique, the synthesized MR image may be registered with a reference body map including various attenuation coefficients (or values) corresponding to different tissues or organs. The attenuation correction data associated with the PET image may be generated based on the registration.

The attenuation correction data for the PET image may delineate the distribution of attenuation coefficients relating to various portions or compositions of the specific subject. The attenuation correction data for the PET image may be in the form of an image, a matrix, a mask, etc. In some embodiments, the attenuation correction data for the PET image may include an attenuation correction image corresponding to the specific subject. The attenuation correction image corresponding to the specific subject may include a 2D attenuation correction image, a 3D attenuation correction image, etc. The attenuation correction image corresponding to the specific subject may represent the specific subject based on a plurality of pixels or voxels. The attenuation coefficients relating to various portions or compositions of the subject may be denoted by the values of the plurality of pixels or voxels in the attenuation correction image. In some embodiments, the attenuation correction data for the PET image may be denoted by a matrix (e.g., a 2D matrix, a 3D matrix, etc.) including a plurality of elements. One of the plurality of elements may denote an attenuation coefficient associated with at least one portion of the specific subject.

The processing device 120 may determine a target PET image of the subject based on the attenuation correction data. In some embodiments, the target PET image may be generated based on the PET image (e.g., PET image data, such as sonogram data) and the attenuation correction data using a PET image reconstruction technique. Exemplary PET image reconstruction techniques may include an iterative reconstruction algorithm, a Fourier slice theorem algorithm, a filtered back projection (FBP) algorithm, a fan-beam reconstruction algorithm, an analytic reconstruction algorithm, or the like, or any combination thereof. In some embodiments, the target PET image may be generated by correcting the PET image based on the attenuation correction data for the PET image. For example, the PET image may be expressed in the form of a first matrix including a plurality of first elements. The attenuation correction data for the PET image may be expressed in the form of a second matrix including a plurality of second elements. One of the plurality of second elements may correspond to one or more of the plurality of first elements. The target PET image may be generated by multiplying each of the plurality of first elements with a corresponding second element.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 510 and operation 520 may be combined into a single operation. As another example, one or more other optional operations (e.g., a storing operation) may be added elsewhere in the process 500. In the storing operation, the processing device 120 may store information and/or data (e.g., the first image, the second image, the trained machine learning model, etc.) associated with the imaging system 100 in a storage device (e.g., the storage device 130) disclosed elsewhere in the present disclosure.

Figure 6:
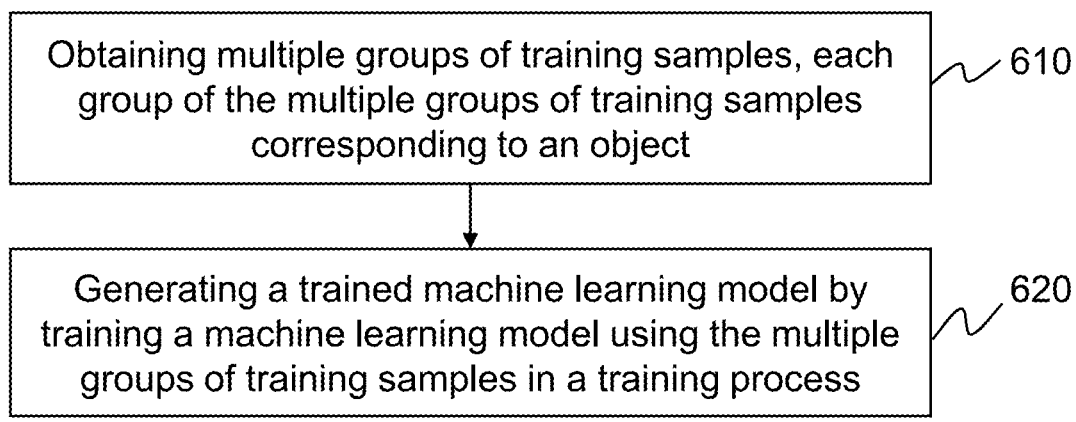
FIG. 6 is a schematic flowchart illustrating an exemplary process for determining a trained machine learning model for image generation according to some embodiments of the present disclosure.

FIG. 6 is a schematic flowchart illustrating an exemplary process for determining a trained machine learning model for image generation according to some embodiments of the present disclosure. In some embodiments, process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the trained machine learning model described in connection with operation 530 in FIG. 5 may be obtained according to the process 600. In some embodiments, the process 600 may be performed by another device or system other than the imaging system 100, e.g., a device or system of a vendor of a manufacturer.

In 610, the processing device 120 (e.g., the obtaining module 450) may obtain multiple groups of training samples. Each group of the multiple groups of training samples may include a reference image and a pair of a third image and a fourth image of different modalities. Each group of the multiple groups of training samples may correspond to an object. In some embodiments, the object corresponding to one or more of the multiple groups of training samples may be a subject as described elsewhere in the present disclosure (e.g., FIG. 5 and the descriptions thereof). The third image may include a complete representation of the object and the fourth image may include a partial representation of the object. For example, the third image may include a first region including a representation of a first portion of the object and a second region including a representation of a second portion of the object. The fourth image may include a third region including a representation of the first portion of the object and a fourth region lacking a representation of the second portion of the object. The reference image may correspond to the fourth image and include a complete representation of the object with respect to the fourth image. The reference image and the fourth image may be of a same modality. The pair of the third image and the fourth image in each group of the multiple groups of training samples may be used as an input of a machine learning model during a training process of the machine learning model. And the reference image corresponding to the fourth image in each group of the multiple groups of training samples may be used as a desired output of the machine learning model during the training process of the machine learning model.

Figure 11:
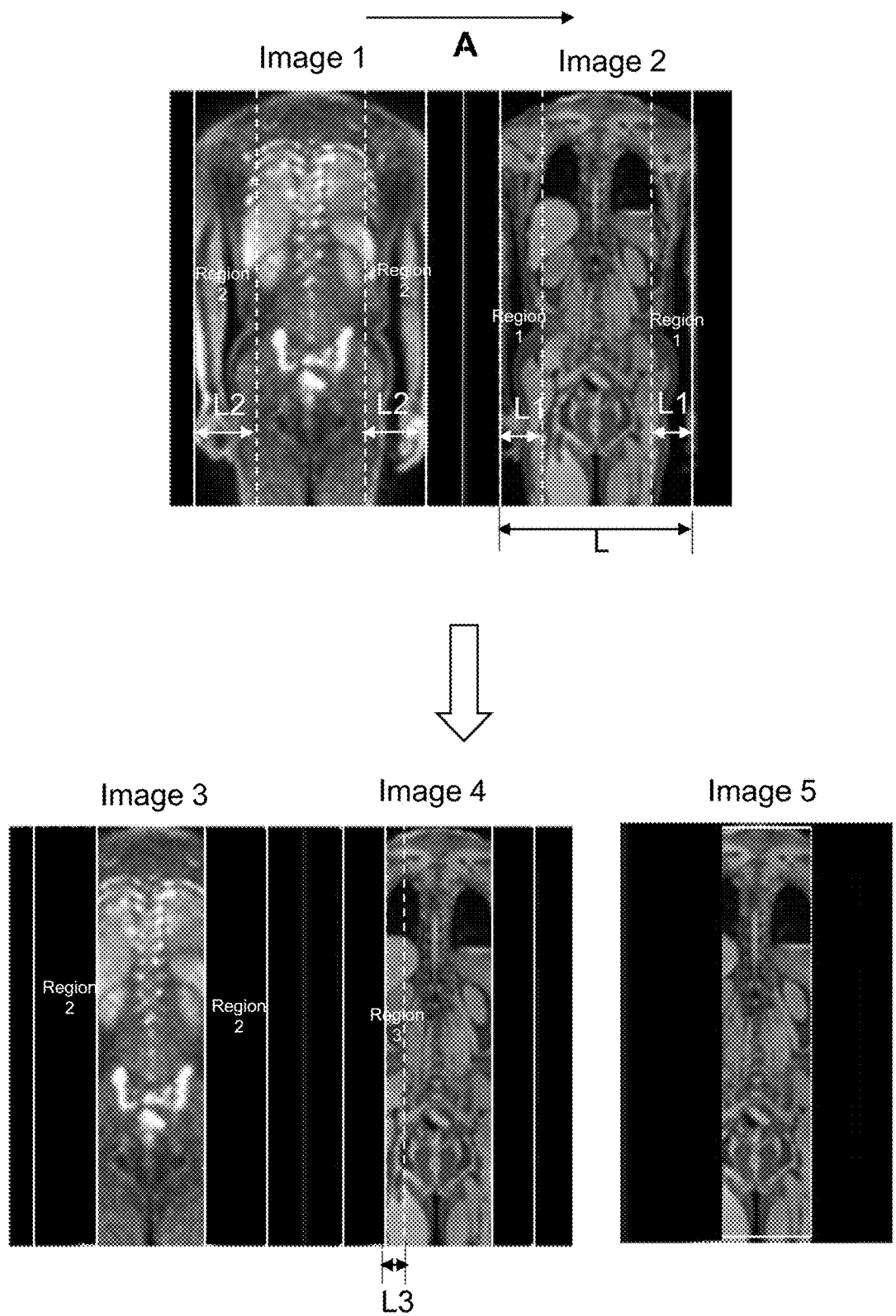
FIG. 11 is a diagram illustrating an exemplary process for acquiring a training sample of a trained machine learning model according to some embodiments of the present disclosure.

In some embodiments, one group of the multiple groups of training samples (the reference image, the third image, and the fourth image) may be determined based on an initial third image and an initial fourth image of different modalities of an initial object. The initial third image may include a complete representation of the initial object. The initial fourth image may include a partial or complete representation of the initial object. The partial representation of the initial object in the initial fourth image may miss a representation of a portion of the initial object (referred to as a missing portion of the initial object). In some embodiments, the processing device 120 may first determine the reference image (e.g., a reference MR image) based on the initial fourth image (e.g., an initial MR image including a truncation artifact). For example, the processing device 120 may determine the reference image (e.g., image 4 as illustrated in FIG. 11) by modifying (e.g., decreasing) pixel values of pixels in one or more sections of the initial fourth image. The one or more sections (e.g., region 1 in image 2 as illustrated in FIG. 11) may belong to a first specific region (e.g., region 3 in image 2 as illustrated in FIG. 9) of the initial fourth image. The first specific region may correspond to a representation of the initial object less the missing portion. As another example, the processing device 120 may designate the initial fourth image as the reference image. The reference image may include a complete representation of an object being at least a portion of the initial object. The processing device 120 may then determine the third image by processing the initial third image according to the reference image. The third image and the reference image may include complete representations of the same object, respectively. For example, the processing device 120 may generate the third image (e.g., image 3 illustrated in FIG. 11) by modifying (e.g., decreasing) pixel values of pixels in one or more sections (e.g., region 2 in image 1 as illustrated in FIG. 11) of the initial third image corresponding to the one or more sections of the initial fourth image (e.g., region 1 in image 2 as illustrated in FIG. 11) and a second specific region (e.g., region 4 and region 4' in image 2 as illustrated in FIG. 9) of the initial fourth image. The second specific region may correspond to the missing portion of the initial object. The processing device 120 may determine the fourth image by processing the reference image. For example, the processing device 120 may generate the fourth image (e.g., image 5 as illustrated in FIG. 11) by modifying (e.g., decreasing) pixel values of pixels in one or more regions (e.g., region 3 in image 4 as illustrated in FIG. 11) of the reference image.

In some embodiments, a truncated third image may be obtained by performing a first truncation operation on the initial third image. The truncated third image may include a representation of a portion of the initial object. A truncated fourth image may be obtained by performing a second truncation operation on the initial fourth image. The truncated fourth image may include a representation of the portion of the initial object represented in the truncated third image. The truncated third image and the truncated fourth image may be designated as the third image and the reference image, respectively. The fourth image may be obtained by performing a third truncation operation on the reference image. More descriptions for determining one of the multiple groups of training sample may be found in FIGS. 7 and 8 and the descriptions thereof.

In 620, the processing device 120 (e.g., the model determination module 470) may generate a trained machine learning model by training a machine learning model using the multiple groups of training samples in a training process. In some embodiments, the trained machine learning model may be constructed based on a convolutional neural network model (CNN), a fully convolutional neural network (FCN) model, a generative adversarial network (GAN) model, or the like, or any combination thereof. More descriptions for determining a training sample for the trained machine learning model may be found in FIGS. 7-8 and the descriptions thereof.

In some embodiments, the machine learning model may include a plurality of parameters, such as architecture parameters, learning parameters, etc. The plurality of parameters may also be referred to as training parameters. One or more parameter values of the plurality of parameters (e.g., the learning parameters) may be altered during the training of the machine learning model using the multiple groups of training samples. The parameter values of the plurality of parameters may be initialized, set, and/or adjusted before the training of the machine learning model to obtain an initialized machine learning model. Exemplary parameters of the machine learning model may include the size of a kernel of a layer, the total count (or number) of layers, the count (or number) of nodes in each layer, a learning rate, a batch size, an epoch, a connected weight between two connected nodes, a bias vector relating to a node, etc.

The machine learning model may be trained based on the multiple groups of training samples using a training algorithm. Exemplary training algorithms may include a gradient descent algorithm, Newton's algorithm, a Quasi-Newton algorithm, a Levenberg-Marquardt algorithm, a conjugate gradient algorithm, or the like, or any combination thereof. In some embodiments, the trained machine learning model may be obtained by performing a plurality of iterations to iteratively update one or more parameter values of the machine learning model. Before the plurality of iterations start, the parameter values of the machine learning model may be initialized. For example, the connected weights and/or the bias vector of nodes of the machine learning model may be initialized by assigning random values in a range, e.g., the range from −1 to 1. As another example, all the connected weights of the machine learning model may be assigned a same value in the range from −1 to 1, for example, 0. As still an example, the bias vector of nodes in the machine learning model may be initialized by assigning random values in a range from 0 to 1. In some embodiments, the parameter values of the machine learning model may be initialized based on a Gaussian random algorithm, a Xavier algorithm, etc.

For each of the plurality of iterations, a specific group of training sample may first be input into the machine learning model. For example, a pair of a specific third image and a specific fourth image in a specific group of training sample may be input into an input layer of the machine learning model, and the reference image corresponding to the specific fourth image may be input into an output layer of the machine learning model as a desired output of the machine learning model. The machine learning model may extract one or more image features (e.g., a low-level feature (e.g., an edge feature, a texture feature), a high-level feature (e.g., a semantic feature), or a complicated feature (e.g., a deep hierarchical feature) included in the specific group of training sample. Based on the extracted image features, the machine learning model may determine a predicted output (i.e., an estimated image) of the specific group of the training sample. For example, the specific third image may include a first region and a second region including representations of a first portion and a second portion of a specific object, respectively. The specific fourth image may include a third region and a fourth region. The third region may include a representation of the first portion and the fourth region may lack a representation of the second portion of the specific object. The predicted output (i.e., an estimated image) may be generated by the machine learning model based on a similarity degree between image features of the first region of the specific third image and the third region of the specific fourth image. For example, the machine learning model may generate the predict output (i.e., an estimated image) such that the similarity degree between image features of the second region of the specific third image and the fourth region of the predict output (i.e., an estimated image) is close to or the same as the similarity degree between the image features of the first region of the specific third image and the third region of the specific fourth image. As used herein, "close to or the same as" may indicate that the deviation of the two similarity degrees, the similarity degree between image features of the second region of the specific third image and the fourth region of the predict output and the similarity degree between the image features of the first region of the specific third image and the third region of the specific fourth image, does not exceed a threshold, e.g., 30%, 20%, or 15%, or 10%, or 5% of one of the two similarity degrees.

The predicted output (i.e., the estimated image) of the specific group of training sample may then be compared with the input reference image of the specific group of training sample based on a cost function. The value of the cost function may be determined based on the extracted image features determined by the machine learning model being trained. The cost function of the machine learning model may be configured to assess a difference between an estimated value (e.g., a predicted output or an estimated image) of the machine learning model and an actual value (e.g., the desired output or the input reference image). If the value of the cost function exceeds a threshold in a current iteration, parameter values of the machine learning model may be adjusted and/or updated in order to decrease the value of the cost function (i.e., the difference between the predicted output and the input specific reference image) to smaller than the threshold. Accordingly, in the next iteration, another group of training sample may be input into the machine learning model to train the machine learning model as described above.

The plurality of iterations may be performed to update the parameter values of the machine learning model until a termination condition is satisfied. The termination condition may provide an indication of whether the machine learning model is sufficiently trained. The termination condition may relate to the cost function or an iteration count of the iterative process or training process. For example, the termination condition may be satisfied if the value of the cost function associated with the machine learning model is minimal or smaller than a threshold (e.g., a constant). As another example, the termination condition may be satisfied if the value of the cost function converges. The convergence may be deemed to have occurred if the variation of the values of the cost function in two or more consecutive iterations is smaller than a threshold (e.g., a constant). As still an example, the termination condition may be satisfied when a specified number (or count) of iterations are performed in the training process. The trained machine learning model may be determined based on the updated parameter values. In some embodiments, the trained machine learning model may be transmitted to the storage device 130, the storage module 440, or any other storage device for storage.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in 610, the processing device 120 may also pre-process the initial third image and the initial fourth image. As another example, one or more other optional operations (e.g., a storing operation) may be added elsewhere in the process 600. In the storing operation, the processing device 120 may store information and/or data (e.g., the multiple groups of training samples, the trained machine learning model, etc.) associated with the imaging system 100 in a storage device (e.g., the storage device 130) disclosed elsewhere in the present disclosure.

Figure 7:
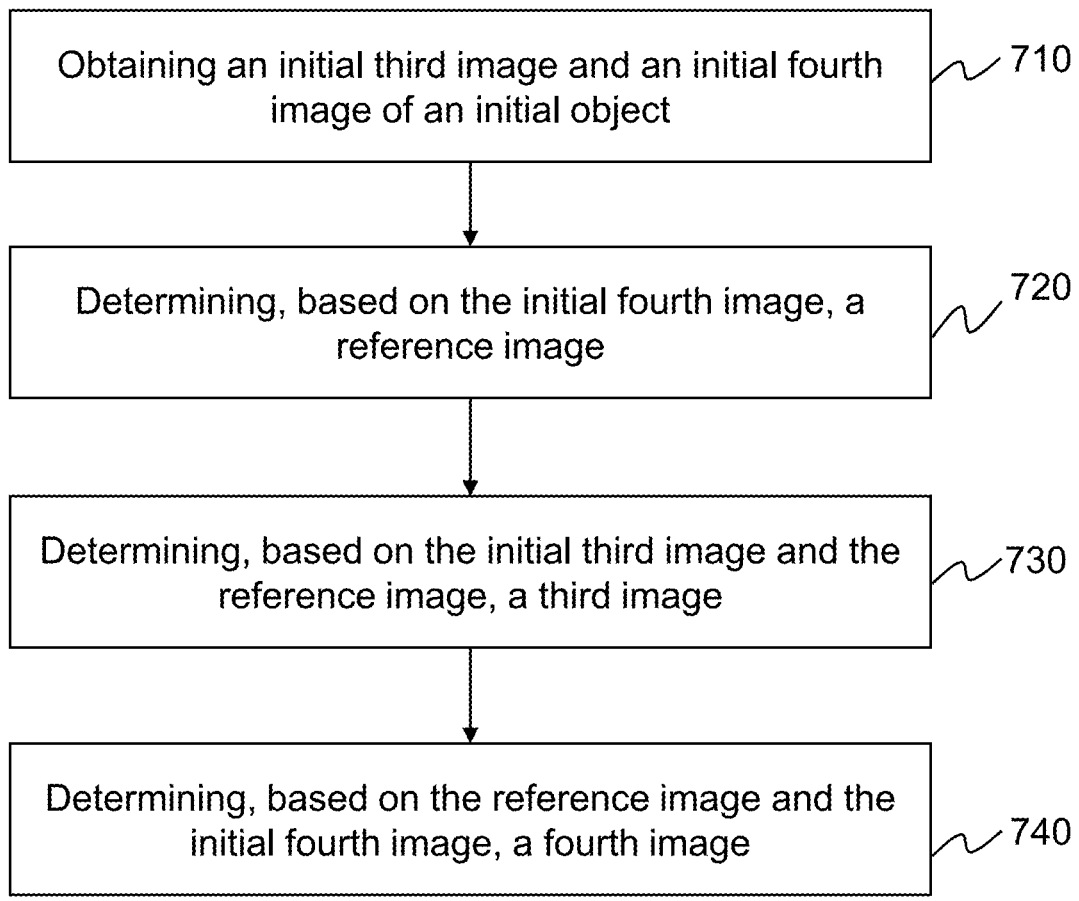
FIG. 7 is a schematic flowchart illustrating an exemplary process for determining a training sample for a trained machine learning model according to some embodiments of the present disclosure.

FIG. 7 is a schematic flowchart illustrating an exemplary process for determining a training sample for a trained machine learning model according to some embodiments of the present disclosure. In some embodiments, process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, a group of training sample in the multiple groups of training samples described elsewhere the present disclosure (e.g., operation 610 illustrated in FIG. 6) may be determined according to the process 700. In some embodiments, the process 700 may be performed by another device or system other than the imaging system 100, e.g., a device or system of a vendor of a manufacturer.

In 710, the processing device 120 (e.g., the obtaining module 450) may obtain an initial third image and an initial fourth image of an initial object. The initial third image may include a plurality of first pixels or voxels. The initial fourth image may include a plurality of second pixels or voxels. Each of the plurality of first pixels or voxels may correspond to one of the plurality of second pixels or voxels. Two corresponding first pixel and second pixel may correspond to or represent the same portion or position of the initial object. The initial object may be referred to as a subject as described elsewhere in the present disclosure (e.g., FIG. 5 and the descriptions thereof). The processing device 120 may obtain the initial third image and the initial fourth image by an imaging device via scanning the initial object. In some embodiments, the processing device 120 may obtain the initial third image and the initial fourth image from the medical device 110, the storage device 130, the storage 220, the storage 390, or any other storage device via the network 150.

The initial third image and the initial fourth image may be in different modalities. For example, the initial third image may be in a first modality and the initial fourth image may be in a second modality. The second modality may be different from the first modality. For example, the initial third image and the initial fourth image may be generated based on same imaging data (e.g., same k-space data) using a first image reconstruction technique and a second image reconstruction technique, respectively, which are two different image reconstruction techniques. Further, the first image reconstruction technique may include a T1 weighted imaging technique and the second image reconstruction technique may include a T2 weighted imaging technique. As another example, the initial third image and the initial fourth image may be acquired, respectively by a first imaging device and a second imaging device which are two different imaging devices. Further, the initial third image and the initial fourth image may be a PET image acquired by a PET device and an MR image acquired by an MRI device, respectively.

The initial third image (e.g., image 1 as illustrated in FIG. 9) may include a complete representation of the initial object. The initial third image may include one or more regions. Each of the one or more regions may include a representation of a portion of the initial object. For example, the initial object represented in the initial third image may include a first portion and a second portion. The initial third image may include a first region (e.g., region 1 in image 1 as illustrated in FIG. 9) including a representation of the first portion of the initial object and a second region (e.g., region 2 and/or region 2' in image 1 as illustrated in FIG. 9) including a representation of the second portion of the initial object. In some embodiments, the initial fourth image may include a complete representation of the initial object. For example, the initial fourth image may include a third region including the representation of the first portion of the initial object and a fourth region including the representation of the second portion of the initial object. In some embodiments, the initial fourth image may include a partial representation of the initial object. The initial fourth image may lack a representation of a portion of the initial object. The portion of the initial object not represented in the initial fourth image may be also referred to as a first missing portion of the initial object. For example, the initial fourth image may include a third region (e.g., region 3 in image 2 as illustrated in FIG. 9) including a representation of the first portion of the initial object and a fourth region (e.g., region 4 and/or region 4' in image 2 as illustrated in FIG. 9) lacking a representation of the second portion of the initial object. The second portion of the initial object may be also referred to as the first missing portion of the initial object. The third region may include a complete representation of the initial object less the first missing portion, i.e., the first portion.

In 720, the processing device 120 (e.g., the sample generation module 460) may determine a reference image based on the initial fourth image. In 730, the processing device 120 (e.g., the sample generation module 460) may determine a third image based on the initial third image and the reference image. An object represented in the third image may be the object represented in the reference image. Each of the third image and the reference image may include a complete representation of the object. In other words, the third image and the reference image may represent the same portion of the initial object. The same portion of the initial object represented in the reference image and the third image may be also referred to as the object.

In some embodiments, the processing device 120 may designate the initial fourth image as the reference image. If the initial fourth image includes a complete representation of the initial object with respect to the initial third image, the reference image may include a complete representation of the initial object. An object represented in the reference image may be the initial object. In operation 730, the processing device 120 may designate the initial third image as the third image. Therefore, the third image and the reference image may include complete representations of the same object (i.e., the initial object). If the initial fourth image (e.g., image 2 as illustrated in FIG. 9 or image 2 as illustrated in FIG. 11) includes a partial representation of the initial object with respect to the initial third image, the reference image may include a partial representation of the initial object. The reference image may represent a portion of the initial object. A missing portion (i.e., the first missing portion as described in operation 710) of the initial object may be not represented in the reference image. The object represented in the reference image may include the initial object less the first missing portion. Therefore, the third image may represent the portion of the initial object represented in the reference image and lack a representation of the first missing portion of the initial object. In operation 730, the processing device 120 may determine the third image by processing the initial third image according to the first missing portion of the initial object. Further, the processing device 120 may remove a representation of the first missing portion of the initial object from the initial third image to obtain the third image. In some embodiments, the portion of the initial object represented in the reference image (i.e., the initial third image, such as image 2 as illustrated in FIG. 9 or image 2 as illustrated in FIG. 11) may correspond to a first specific region image 1 as illustrated in FIG. 9 of the reference image. The first missing portion of the initial object not represented in the reference image may correspond to a second specific region (e.g., region 4 and/or region 4' in image 2 as illustrated in FIG. 9) of the reference image. The processing device 120 may determine the third image by processing the initial third image according to the second specific region (e.g., region 4 and/or region 4' in image 2 as illustrated in FIG. 9) of the reference image. For example, the processing device 120 may determine a specific region (e.g., region 2 and/or region 2' in image 1 as illustrated in FIG. 9) in the initial third image according to the second specific region (e.g., region 4 and/or region 4' in image 2 as illustrated in FIG. 9) of the reference image. The specific region (e.g., region 2 and/or region 2' in image 1 as illustrated in FIG. 9) in the initial third image may correspond to the second specific region (e.g., region 4 and/or region 4' in image 2 as illustrated in FIG. 9) in the reference image. The processing device 120 may obtain the third image by decreasing pixel values of pixels in the specific region (e.g., region 2 and/or region 2' in image 1 as illustrated in FIG. 9) of the initial third image (e.g., image 1 as illustrated in FIG. 9). Further, the processing device 120 may modify (e.g., decrease) the pixel values of pixels in the specific region of the initial third image to or close to value "0" to obtain the third image. As used herein, the specific region in the initial third image corresponding to the second specific region in the reference image may refer to that two corresponding regions in the initial third image and in the reference image correspond to the same physical location of the initial third image and the reference image.

In some embodiments, the processing device 120 may determine the reference image (e.g., image 4 as illustrated in FIG. 11) by removing a portion of a representation of the initial object from the initial fourth image (e.g., image 2 as illustrated in FIG. 11). In other words, the processing device 120 may remove signals or information in one or more regions (e.g., region 1 in image 2 as illustrated in FIG. 11) of the initial fourth image (e.g., image 2 as illustrated in FIG. 11) to obtain the reference image. The object represented in the reference image may include the initial object less a second missing portion. If the initial fourth image includes a partial representation of the initial object, the second missing portion of the initial object may include the first missing portion of the initial object. If the initial fourth image includes a complete representation of the initial object, the second missing portion of the initial object may be any portion of the initial object. In operation 730, the processing device 120 may determine the third image by processing the initial third image according to the second missing portion of the initial object. Further, the processing device 120 may remove a representation of the second missing portion of the initial object from the initial third image to obtain the third image. Therefore the third image and the reference image may include complete representation of the same object.

For example, if the initial fourth image includes the complete representation of the initial object, the processing device 120 may determine one or more specific regions in the initial fourth image. The processing device 120 may modify (e.g., decrease) pixel values of pixels to or close to value "0" in the one or more specific regions of the initial fourth image to obtain the reference image. The second missing portion of the initial object may correspond to the one or more specific regions of the reference image. The one or more specific regions of the reference image may lack the representation of the second missing portion. In operation 730, the processing device 120 may determine one or more specific regions in the initial third image. The one or more specific regions in the initial third image may correspond to the one or more specific regions in the initial fourth image. The processing device 120 may modify (e.g., decrease) pixel values of pixels to or close value "0" in the one or more specific regions of the initial third image to obtain the third image. The one or more specific regions of the third image may lack the representation of the second missing portion.

As another example, if the initial fourth image (e.g., image 2 as illustrated in FIG. 11) includes a partial representation of the initial object, the processing device 120 may determine one or more sections (e.g., region 1 in image 2 as illustrated in FIG. 11) in a specific region (i.e., the first specific region, e.g., region 3 in image 2 as illustrated in FIG. 9) of the initial fourth image. The first specific region of the initial fourth image may correspond to the initial object less the first missing portion. The second specific region (e.g., region 4 and/or region 4' in image 2 as illustrated in FIG. 9) of the initial fourth image may correspond to the first missing portion of the initial object. The processing device 120 may modify (e.g., decrease) pixel values of pixels to or close to value "0" in the one or more sections in the first specific region (e.g., region 1 in image 2 as illustrated in FIG. 11) of the initial fourth image to obtain the reference image (e.g., image 4 as illustrated in FIG. 11). In operation 730, the processing device 120 may determine one or more specific regions (e.g., region 2 in image 1 as illustrated in FIG. 11) in the initial third image (e.g., image 1 as illustrated in FIG. 11). The one or more specific regions(e.g., region 2 in image 1 as illustrated in FIG. 11) in the initial third image may correspond to the one or more sections (e.g., region 1 in image 2 as illustrated in FIG. 11) in the first specific region (e.g., region 3 and/or region 3' in image 2 as illustrated in FIG. 9) of the initial fourth image and the second specific region of the initial fourth image (e.g., region 4 and/or region 4' in image 2 as illustrated in FIG. 9). The processing device 120 may modify (e.g., decrease) pixel values of pixels to or close to value "0" in the one or more specific regions of the initial third image to obtain the third image. The one or more specific regions of the third image may lack representation of the second missing portion of the initial object.

As a further example, if the initial fourth image includes the third region including the representation of the first portion of the initial object and the fourth region lacking the representation of the second portion of the initial object, the first specific region of the initial fourth image may be the third region of the initial fourth image. The second specific region of the initial fourth image may be the fourth region of the initial fourth image. The processing device 120 may decrease pixel values of pixels to or close to value "0" in the one or more sections in the third region (i.e., the first specific region) of the initial fourth image to obtain the reference image. The second missing portion of the initial object not represented in the reference image may include the second portion of the initial object and a portion of the first portion corresponding to the one or more sections in the third region (i.e., the first specific region). The second missing portion of the initial object may correspond to a specific region of the reference image. The specific region of the reference image may correspond to the fourth region (i.e., the second specific region) of the initial fourth image and the one or more sections of the third region (i.e., the first specific region) of the initial fourth image. In operation 730, the initial third image may include the first region representing the first portion of the initial object and the second region representing the second portion of the initial object. The reference image may include the third region including the partial representation of the first portion of the initial object and the fourth region lacking the representation of the second portion of the initial object. The reference image may include one or more sections in the third region lacking a representation of a portion of the first portion of the initial object. The processing device 120 may determine one or more sections in the first region of the initial third image corresponding respectively to the one or more sections in the third region of the reference image. The processing device 120 may obtain the third image by modifying (e.g., decreasing) pixel values of pixels in the second region of the initial third image and decreasing pixel values of pixels in the one or more sections in the first region of the initial third image. As used herein, one section in the first region corresponding to one section in the third region may refer to that the two sections corresponding to the same physical position of the initial third image and the reference image and corresponding to a same portion or position of the initial object.

In 740, the processing device 120 (e.g., the sample generation module 460) may determine a fourth image based on the reference image and the initial fourth image. In some embodiments, the processing device 120 may determine a processed reference image by modifying (e.g., decreasing) pixel values of pixels in one or more sections of the reference image. The processing device 120 may designate the processed reference image as the fourth image.

In some embodiments, the processing device 120 may determine the third image, the fourth image, and the reference image as a group of training samples for training a machine learning model. In some embodiments, the portion of the initial object represented in the third image and/or the reference image may also be referred to as an object associated with multiple groups of training samples as described in FIG. 6. The object may be at least a portion of the initial object less the missing portion of the initial object. In some embodiments, the processing device 120 may transmit the training sample the storage device 130, the storage 220, the storage 390, or any other storage device via the network 150.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 730 and operation 740 may be combined into a single operation. As another example, one or more other optional operations (e.g., a storing operation) may be added elsewhere in the process 700. In the storing operation, the processing device 120 may store information and/or data (e.g., the third image, the fourth image, the reference image, etc.) associated with the imaging system 100 in a storage device (e.g., the storage device 130) disclosed elsewhere in the present disclosure.

Figure 8:
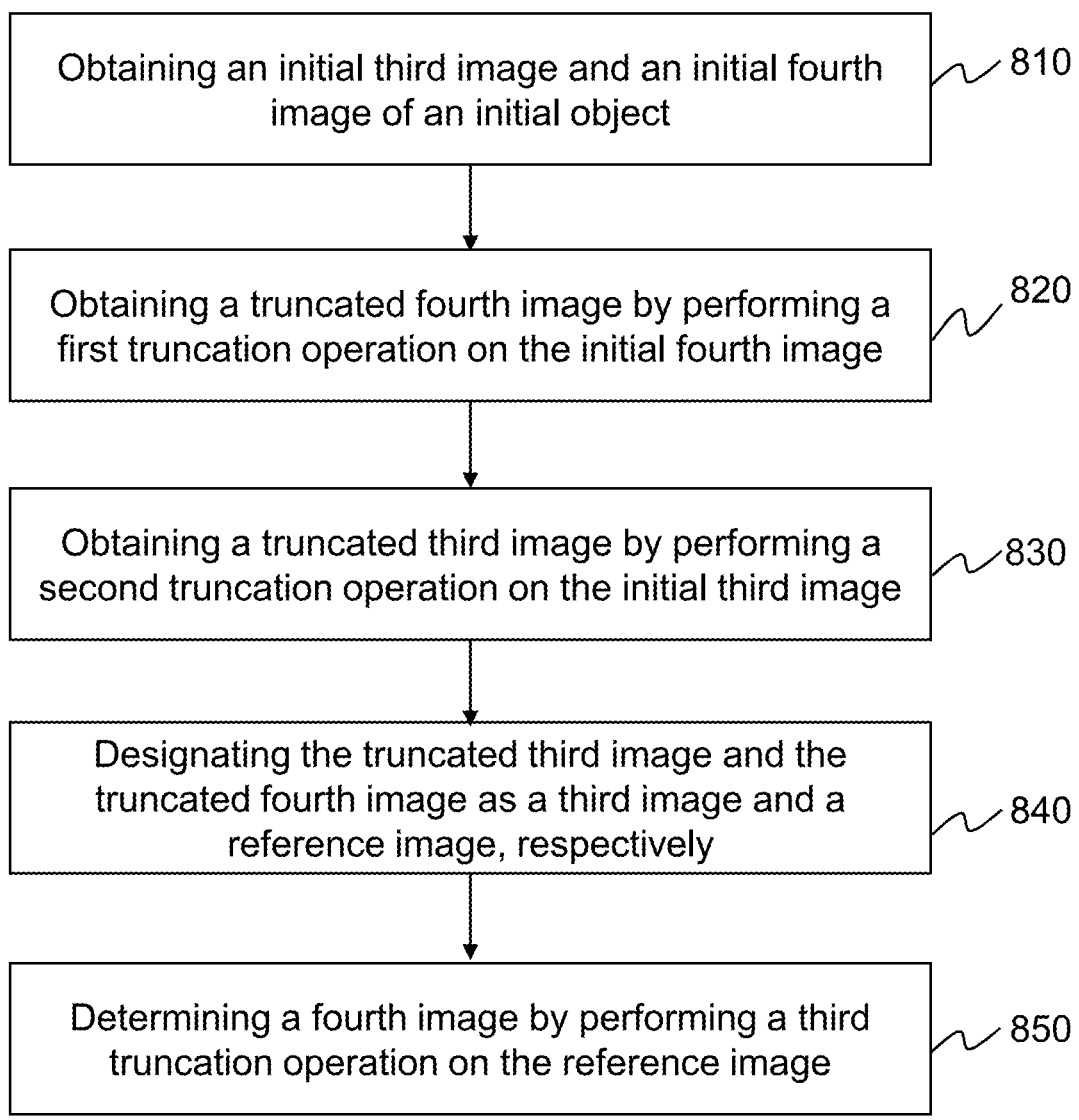
FIG. 8 is a schematic flowchart illustrating an exemplary process for determining a training sample for a trained machine learning model according to some embodiments of the present disclosure.

FIG. 8 is a schematic flowchart illustrating an exemplary process for determining a training sample for a trained machine learning model according to some embodiments of the present disclosure. In some embodiments, process 800 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, a group of training sample in the multiple groups of training samples described elsewhere the present disclosure (e.g., operation 610 illustrated in FIG. 6) may be determined according to the process 800. In some embodiments, the process 800 may be performed by another device or system other than the imaging system 100, e.g., a device or system of a vendor of a manufacturer.

In 810, the processing device 120 (e.g., the obtaining module 410) may obtain an initial third image and an initial fourth image of an initial object.

The initial third image may include a complete representation of the initial object. The initial third image may include one or more regions. Each of the one or more regions may include a representation of a portion of the initial object. For example, the initial object represented in the initial third image may include a first portion and a second portion. The initial third image may include a first region including a representation of the first portion of the initial object and a second region including a representation of the second portion of the initial object. In some embodiments, the initial fourth image may include a complete representation of the initial object. For example, the initial fourth image may include a third region including the representation of the first portion of the initial object and a fourth region including the representation of the second portion of the initial object. In some embodiments, the initial fourth image may include a partial representation of the initial object. The initial fourth image may lack a representation of a portion of the initial object. The portion of the initial object not represented in the initial fourth image may be also referred to as a first missing portion of the initial object with respect to the initial fourth image. For example, the initial fourth image may include a third region including a representation of the first portion of the initial object and a fourth region lacking a representation of the second portion of the initial object. The second portion of the initial object may be also referred to as the first missing portion of the initial object with respect to the initial fourth image. The third region may include a complete representation of the initial object less the first missing portion (i.e., the first portion). In some embodiments, lacking the representation of the second portion of the initial object may be caused by a truncation artifact, a metal artifact, etc. In some embodiments, the initial third image and the initial fourth image may be acquired by two different image devices (e.g., a PET device and an MRI device). More descriptions about the initial third image and the initial fourth image may be found elsewhere in the present disclosure (e.g. FIG. 7 and the descriptions thereof).

In 820, the processing device 120 (e.g., the sample generation module 460) may obtain a truncated fourth image by performing a first truncation operation on the initial fourth image. The truncated fourth image may include a complete representation of an object. The object may be at least a portion of the initial object.

In some embodiments, if the initial fourth image includes the third region including the representation of the first portion of the initial object and the fourth region lacking the representation of the second portion of the initial object, the truncated fourth image may include a representation of at least a portion of the first portion of the initial object. In some embodiments, a missing portion of the first portion of the initial object may be not represented in the truncated fourth image. For example, the third region of the initial fourth image may include a first section and a second section. The first section may include a representation of the portion of the first portion of the initial object. The second section may lack a representation of the missing portion of the first portion of the initial object. The truncated fourth image may lack the representation of the second portion of the initial object and the missing portion of the first portion of the initial object. The second portion of the initial object and the missing portion of the first portion of the initial object may also be referred to as a second missing portion of the initial object with respect to the truncated fourth image.

As used herein, a truncation operation on an initial image of an initial object may be configured to remove or extract information or signals in a specific region of the initial image to obtain a truncated image of an object that may be a portion of the initial object less a missing portion of the initial object. A truncation operation may be defined by a truncation direction, a truncation size, a truncation area, or the like, or any combination thereof. In some embodiments, the truncation size may be referred to as a length of the specific region where information or signals in a specific region of an image is removed along the truncation direction. The truncation area may refer to the specific region where information or signal is removed by the truncation operation. Exemplary truncation directions may include a radial direction, an axial direction (e.g., a horizontal axis direction of an image, a vertical axis direction of an image), etc. As used herein, a radial direction of an image may refer to a direction passing through the center of the image.

The first truncation operation may include a first truncation size (or first truncation area), a first truncation direction, etc. The first truncation size may be less than a length of the first region of the initial fourth image along the first truncation direction. For example, the first truncation direction may include a horizontal direction (e.g., the horizontal direction denoted by arrow A in FIG. 11) of the initial fourth image (e.g., image 2 in FIG. 11). The first truncation size (e.g., L1 as shown in image 2 in FIG. 11) may be smaller than the length (e.g., L as shown in image 2 in FIG. 11) of the third region of the initial fourth image along the horizontal direction of the initial fourth image. The truncated fourth image (e.g., Image 4 as shown in FIG. 11) may lack the representation of the missing portion (e.g., region 1 in image 2 as shown in FIG. 11) of the first portion of the initial object. In some embodiments, the first truncation operation may include using an imcrop function, a getrect function, a ndgrid function, or the like, or any combination thereof.

In 830, the processing device 120 (e.g., the sample generation module 460) may obtain a truncated third image by performing a second truncation operation on the initial third image. The truncated third image may include a representation of the portion of the initial object represented in the truncated fourth image. In other words, the truncated fourth image and the truncated third image may represent the same portion of the initial object. For example, the truncated third image may include a first specific region and a second specific region. The first specific region may include a representation of a portion of the first portion of the initial object represented in the truncated fourth image. The second specific region may lack the representation of the second portion of the initial object and the missing portion of the first portion of the initial object (i.e., the second missing portion of the initial object with respect to the truncated fourth image).

In some embodiments, the second truncation operation may include a second truncation direction, a second truncation size, etc. The second truncation direction in the second truncation operation may be the same as the first truncation direction in the first truncation operation. For example, if the first truncation direction in the first truncation operation is the radial direction of the initial fourth image, the second truncation direction in the second truncation operation is the radial direction of the initial third image. As another example, if the first truncation direction in the first truncation operation is the axis direction (e.g., horizontal direction denoted by arrow A in FIG. 11) of the initial fourth image, the second truncation direction in the second truncation operation is the axis direction (e.g., horizontal direction denoted by arrow A in FIG. 11) of the initial third image. The second truncation size in the second truncation operation may be different from the first truncation size in the first truncation operation. For example, the second truncation size (e.g., L2 as shown in image 1 in FIG. 11) may exceed the first truncation size (e.g., L1 as shown in image 2 in FIG. 11). The second truncation size in the second truncation operation may be determined based on the first truncation size in the first truncation operation. The greater the first truncation size is, the greater the second truncation size may be, such that the fourth truncated image and the truncated third image may represent the same portion of the initial object. In some embodiments, the second truncation operation and the first truncation operation may include using identical or different truncation techniques. For example, the first truncation operation may use an imcrop function, and the second truncation operation may use a getrect function. As another example, the first truncation operation and the second truncation operation may use an imcrop function.

In 840, the processing device 120 (e.g., the sample generation module 460) may designate the truncated third image and the truncated fourth image as a third image and a reference image, respectively. In some embodiments, the processing device 120 may store the third image and the reference image into a storage device (e.g., the storage device 130, the storage 220, the storage 390 or any other storage device) for storage. The third image and the reference image may include representations of the same portion of the initial object, respectively. In some embodiments, the same portion of the initial object may be referred to as an object represented in the reference image and the third image associated with a group of training samples as described elsewhere in the present disclosure (e.g., FIG. 6 and the descriptions thereof).

In 850, the processing device 120 (e.g., the sample generation module 460) may determine a fourth image by performing a third truncation operation on the reference image. The fourth image may include a representation of a portion of the object represented in the truncated third image (or the third image) and/or the truncated fourth image (or the reference image).

The third truncation operation may include a third truncation direction, a third truncation size, etc. The third truncation direction may be the same as or different from the first truncation direction or the second truncation direction. The third truncation direction in the third truncation operation may be any direction of the reference image (or the truncated fourth image). For example, the third truncation direction in the third truncation operation may be the radial direction of the reference image (or the truncated fourth image). As another example, the third direction in the third truncation operation may be the axial direction of the reference image (or the truncated fourth image). The third truncation size may be the same as or different from the first truncation size or the second truncation size. The third truncation size (e.g., L3 as shown in Image 4 in FIG. 11) in the third truncation operation may be any size that smaller than the length of a region including a complete representation of the portion of the initial object represented in the reference image along the third truncation direction. In some embodiments, a truncation technique used in the third truncation operation may be the same as or different from the truncation technique used in the first truncation operation and/or the second truncation operation. The truncation techniques used in the first truncation operation, the second truncation operation and the third truncation operation may be the same as or different from each other.

In some embodiments, the reference image, the third image, and the fourth image may be determined as one group of a training sample for training a machine learning model. For example, the third image and the fourth image may be used as an input of the machine learning model and the reference image may be used as a desired output of the machine learning model. In some embodiments, different groups of training samples may be obtained by adjusting truncation sizes and/or truncation directions of the first truncation operation, the second truncation operation, and the third truncation operation. For example, if the first truncation size of the first truncation operation, the second truncation size of the second truncation operation, and the third truncation size of the third truncation operation are "a", "b", and "c", respectively. A group of training samples may be obtained. If the first truncation size of the first truncation operation, the second truncation size of the second truncation operation, and the third truncation size of the third truncation operation are "x", "y", and "z", respectively. Another group of training samples may be obtained. In some embodiments, the training samples may be transmitted to the storage device 130, the storage 220, the storage 390, or any other storage device via the network 150.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, the operation 810 and the operation 820 may be combined into a single operation to obtain the truncated third image and the truncated fourth image. As another example, one or more other optional operations (e.g., a storing operation) may be added elsewhere in the process 800. In the storing operation, the processing device 120 may store information and/or data (e.g., the truncated third image and the truncated fourth image, the reference image, etc.) associated with the imaging system 100 in a storage device (e.g., the storage device 130) disclosed elsewhere in the present disclosure. In some embodiments, operation 820 may be omitted. The processing device 120 may designate the initial fourth image as the reference image.

EXAMPLES

The following examples are provided for illustration purposes and are not intended to limit the scope of the present disclosure.

Example 1

Exemplary a PET Image and an MR Image Corresponding to the Same Portion of the Body of a Patient FIG. 9 shows exemplary images of different modalities according to some embodiments of the present disclosure. As shown in FIG. 9, image 1 and image 2 are a PET image and an MR image representing a portion of a patient, respectively. Image 2 includes truncation artifacts causing image 2 to lack a representation of edge portions (e.g., arm edges) of the patient that are shown in image 1. For example, image 1 includes region 1, region 2, and region 2' constituting a complete representation of a portion of interest of the patient. Image 2 includes region 3, region 4, and region 4'. Region 4 and region 4' in image 2 lack representations of the edge portions (e.g., edges of the arm of the patient).

Example 2

Figure 10:
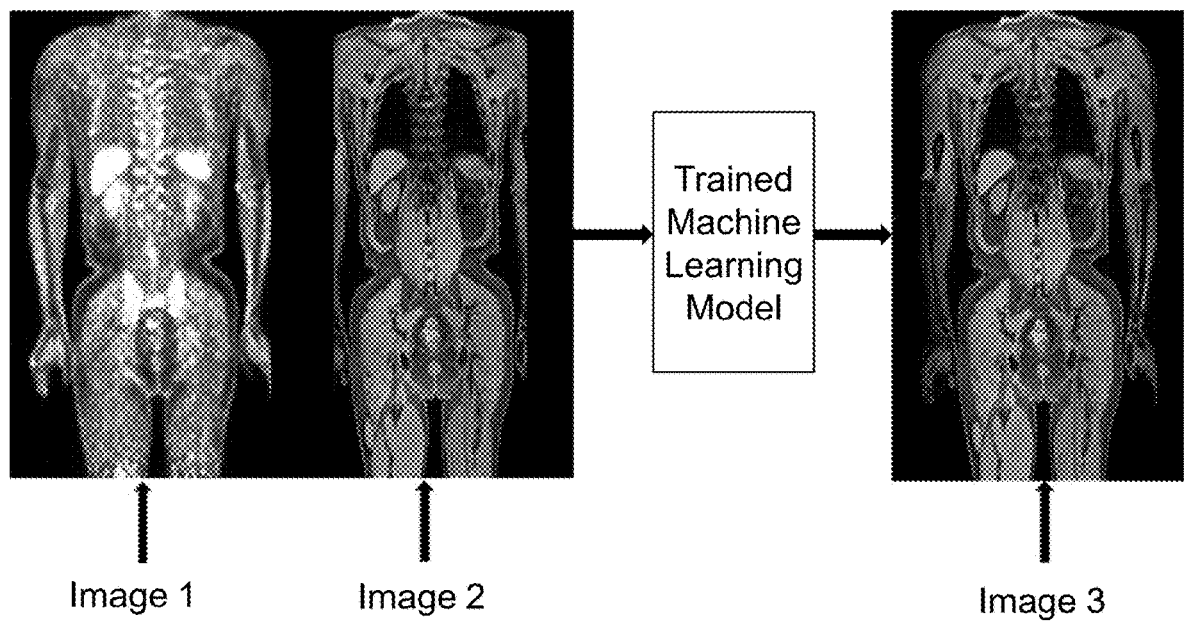
FIG. 10 is an exemplary diagram showing an exemplary process for determining a truncation compensated MR image using a trained machine learning model according to some embodiments of the present disclosure.

Exemplary Process for Generating a Synthesized MR Image Including a Complete Representation of a Subject Using a Trained Machine Learning Model FIG. 10 is an exemplary diagram showing an exemplary process for determining a truncation compensated image (i.e., synthesized MR image) using a trained machine learning model according to some embodiments of the present disclosure. As shown in FIG. 10, image 1 and image 2 are a PET image and an MR image of the same portion of interest of a patient, respectively. Image 1 includes a complete representation of the same portion of interest of the patient. Image 2 includes a partial representation of the same portion of interest of the patient which is caused by truncation artifacts. Image 2 lacks a representation of the edge portions (e.g., arm edges) of the same portion of interest of the patient. Image 1 and image 2 are input into the trained machine learning model as described elsewhere in the present disclosure (e.g., FIGS. 5 and 6, and the descriptions thereof). The trained machine learning model may output a synthesized MR image (i.e., image 3) corresponding to the MR image (i.e., image 2). The synthesized MR image (i.e., image 3) has a complete representation of the same portion of interest of the patient compared with the MR image.

Example 3

Exemplary a Training Sample of a Trained Machine Learning Model

FIG. 11 is a diagram illustrating an exemplary process for acquiring a training sample of a trained machine learning model according to some embodiments of the present disclosure. As illustrated in FIG. 11, image 1 is a PET image (e.g., the initial third image as described in FIG. 7 or FIG. 8) and image 2 is an MR image (e.g., the initial fourth image as described in FIG. 7 or FIG. 8). Image 2 has a truncation artifact causing image 2 to lack a representation of a portion of the subject (e.g., a patient's body) with respect to image 1. Image 4 (e.g., the reference image as described in FIG. 7 or FIG.8) was obtained by removing information or signals in region 1 of image 2. For example, image 4 may be obtained by performing a first truncation operation on region 1 of image 2. As another example, image 4 may be obtained by decreasing pixel values of pixels in region 1 of image 2 to value 0. Image 3 (e.g., the third image as described in FIG. 7 or FIG. 8) was obtained by removing information or signals in region 2 of image 1. For example, image 3 was obtained by performing a second truncation operation on region 2 of image 1. As another example, image 3 may be obtained by decreasing pixel values of pixels in region 2 of image 1 to value 0. Image 3 and image 4 may represent the same portion of the subject (e.g., a patient's body). Image 5 (e.g., the fourth image as described in FIG. 7 or FIG.8) was obtained by removing information or signals in region 3 of image 4. For example, image 5 may be obtained by performing a third truncation operation on region 3 of image 4. As another example, image 5 may be obtained by decreasing pixel values of pixels in region 3 of image 4 to value 0. Image 3 and image 5 may be used as an input of a machine learning model and image 4 (i.e., reference image) may be used as a desired output of the machine learning model in a training process. More descriptions for acquiring a training sample may be found elsewhere in the present disclosure (e.g., FIG. 7 and FIG. 8 and the descriptions thereof).

Example 4

Exemplary Process for Training a Machine Learning Model

Figure 12:
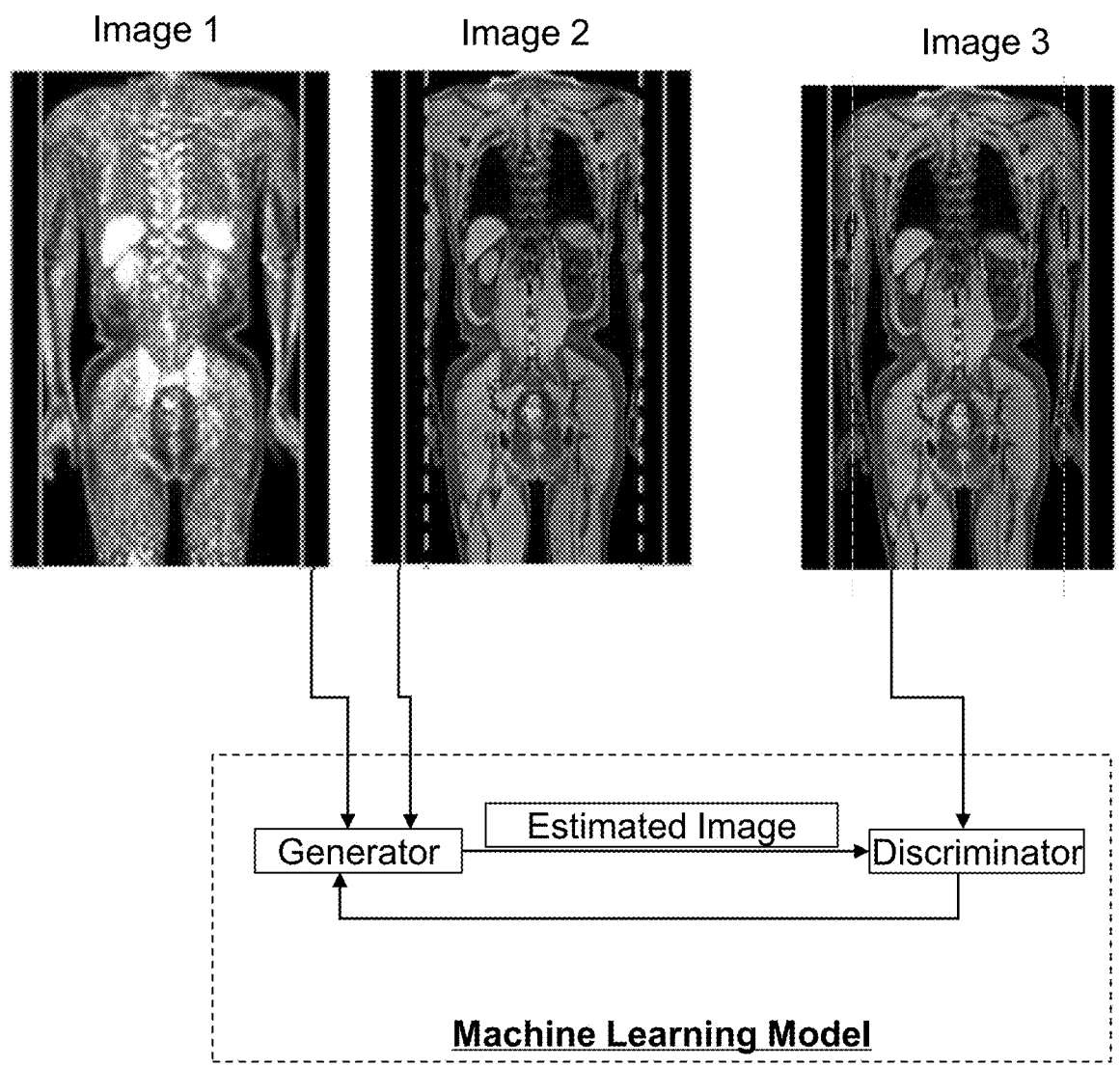
FIG. 12 is a diagram illustrating an exemplary process for determining a trained machine learning model according to some embodiments of the present disclosure.

FIG. 12 is a diagram illustrating an exemplary process for determining a trained machine learning model according to some embodiments of the present disclosure. The trained machine learning model may be obtained as described elsewhere in the present disclosure (e.g., FIG. 6 and the descriptions thereof). As shown in FIG. 12, the trained machine learning model is constructed based on a generative adversarial network (GAN) model. The GAN model may include a generator and a discriminator connected with the generator. The generator may include a first neural network (also referred to as a generative network) that has a first set of parameters to be optimized by training. The generator may be configured to generate an estimated image based on one or more inputted images. The generator may send the estimated image to the discriminator. The discriminator may include a second neural network (also referred to as a discriminative network) that has a second set of parameters to be optimized by training. The discriminator may be configured to evaluate the estimated image generated by the generator.

The GAN model may be obtained by performing a plurality groups of iterations to iteratively update the first set of parameters and the second set of parameters. For a first group of iterations, the second set of parameters may be fixed when training the first set of parameters. A group of training samples including a reference image and a pair of a third image and a fourth image as described elsewhere in the present disclosure (e.g., FIG. 5 and the descriptions thereof) may be input into the GAN model. For example, a specific third image and a specific fourth image of a group of training sample may be input into the generator, and a reference image of the group of training sample may be input into the discriminator. The generator may output an estimated image based on the inputted specific third image and the specific fourth image, the discriminator may receive the estimated image and generate a quality metric based on a comparison of the estimated image with the reference image (i.e., a desired image) using the fixed second set of parameters. The quality metric may indicate a degree of similarity or difference between an output image (e.g., the estimated image) of the generator and the reference image inputted into the discriminator. The discriminator may output a value of the quality metric to the generator. If the value of the quality metric exceeds a threshold in a current iteration, the first set of parameters may be adjusted and/or updated to cause the value of the quality metric (e.g., the degree of difference between the estimated output image and the input specific reference image) smaller than the threshold. Accordingly, in the next iteration, another group of training sample may be input into the GAN model to train the generator as described above. Then multiple iterations may be performed to update the first set of parameters until the discriminator may be unable to distinguish the estimated output image and the inputted reference image (e.g., the degree of difference between the updated output image of the generator and the specific reference image inputted into the discriminator, for example, close to 0%). Then the second set of parameters may be updated and/or adjusted to cause the discriminator can accurately distinguish the estimated output image and the inputted specific reference image. Accordingly, in the next group of iterations, the training of the updated first set of parameters and the updated second set of parameters may be performed as described above. The plurality groups of iterations may be performed to update the first set of parameters and the second set of parameters until the discriminator cannot distinguish the reference image and the estimated image generated by the generator. The training of the GAN model may be used to decrease the error rate of the generator so that the generated de-estimated image approaches the reference image. The training of the GAN model may be used to increase the error rate of the discriminator so that the discriminator cannot distinguish the reference image and the estimated image generated by the generator.

Figure 13:
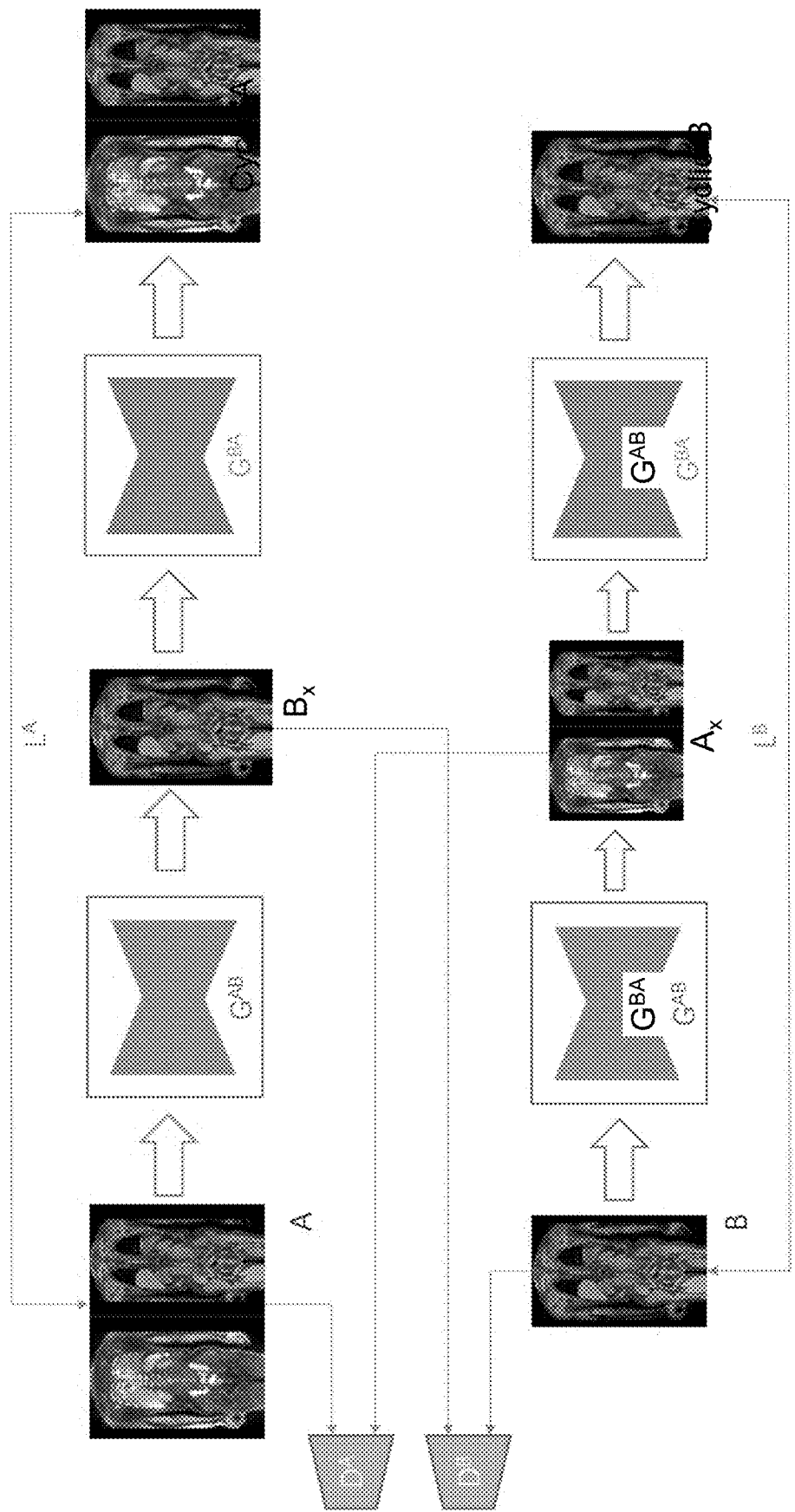
FIG. 13 is a schematic diagram illustrating an exemplary cycle generative adversarial network (GAN) model according to some embodiments of the present disclosure.

During a training process of the GAN model, a training sample including image 1 and image 2 as shown in FIG. 12 may be inputted into the generator. Image 1 may be a PET image including a complete representation of a portion of a patient's body. Image 2 may be an MR image including a partial representation of the portion of the patient's body caused by, for example, a truncation artifact. The generator may generate an estimated image including a complete representation of the portion of the patient's body with respect to the MR image based on a similarity degree between the PET image and the MR image. The estimated image may be transmitted to the discriminator. The discriminator may compare the estimated image with image 3 as the reference image to distinguish the estimated image with image 3. Image 3 may include a complete representation of the portion of the patient's body with respect to the MR image (i.e., image 2). The discriminator may generate a quality metric indicating a degree of similarity or difference between the estimated image and image 3 using the second set of parameters. If the quality metric is less than a threshold, the generator may update the first set of parameters based on the quality metric and produce an updated output image using the updated first set of parameters Example 5 Exemplary cycle generative adversarial network (GAN) model FIG. 13 is a schematic diagram illustrating an exemplary cycle generative adversarial network (GAN) model according to some embodiments of the present disclosure. The cycle GAN model 1300 may include two generators and two discriminators as described in FIG. 12. For illustration purposes, the cycle GAN model 1300 may include generators $G^{AB}$ and $G^{BA}$, and discriminators $D^A$ and $D^B$ as illustrated in FIG. 13. A group of training sample may include a PET image, a truncated MR image, and a reference MR image. The PET image may include a complete representation of a portion of a patient's body. A truncated MR image may include a partial representation of the portion of the patient's body caused by truncation artifacts. The reference MR image (i.e., image B) may include a complete representation of the portion of the patient's body with respect to the truncated MR image.

The PET image and the truncated MR image (also may be referred to as image A) may be inputted into the generator $G^{AB}$ together to generate a first estimated MR image (i.e., image $B_x$). The first estimated MR image may be compared with the reference MR image (i.e., image B) based on a first adversarial loss function of the discriminator $D^B$. The first adversarial loss function may be denoted as $L(G^{AB}, D_B, A, B_X)$. As used herein, an adversarial loss function of a discriminator may be configured to assess a difference between an estimated value (e.g., the first estimated MR image or image $B_X$) of a generator (e.g., the generator $G^{AB}$) and an actual value (e.g., the reference MR image or image B). The first estimated MR image may then be input into the generator $G^{BA}$ to generate a first predicted PET image and a first predicted truncated MR image (also may be referred to as image cyclic A). A difference between the first predicted PET image in image cyclic A and the PET image in image A, and a difference between the first predicted truncated MR image in image cyclic A and the MR image in image A may be assessed based on a first cycle consistency loss function denoted as $L_A(G^{AB}, G^{BA})$.

Similarly, the reference MR image (or image B) may be inputted into the generator $G^{BA}$ to generate a second predicted PET image and a second predicted truncated MR image (also may be referred to as image $A_x$). The second predicted PET image and the second predicted truncated MR image may then be compared with the PET image and the truncated MR image based on a second adversarial loss function of the discriminator $D^A$. The second adversarial loss function may be denoted as $L(G^{BA}, D_A, B, A_X)$. The second predicted PET image and the second predicted truncated MR image may be transmitted to the generator $G^{AB}$ to generate a second estimated MR image (or image cyclic B). A difference between the second estimated MR image (or image cyclic B) and the reference MR image (or the image B) may be assessed based on a second cycle consistency loss function denoted as $L_B(G^{AB}, G^{BA})$. The first cycle consistency loss function and the second cycle consistency loss function may be a same function denoted as $L_{cyc}(G^{AB}, G^{BA})$.

Accordingly, an objective function of the cycle GAN model may be described as:

$$L(G^{AB}, G^{BA}, D_A, D_B) = L(G^{AB}, D_B, A, B_X) + L(G^{BA}, D_A, B, A_X) + \lambda L_{cyc}(G^{AB}, G^{BA}), \quad (1)$$

where $\lambda$ may be a real number greater than 0. The cycle GAN model may be trained based on the objective function. For example, if the value of the objective function satisfies a condition, the training process of the cycle GAN model may terminate. If the value of the objective function does not satisfy the condition, the parameters of the cycle GAN model may be updated further by repeating the process as described above using another group of training sample.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
   at least one storage device storing executable instructions, and
   at least one processor in communication with the at least one storage device, when executing the executable instructions, causing the system to perform operations including:
      obtaining a first image of a subject of a first modality, the first image including a first region and a second region, the first region including a representation of a first portion of the subject, and the second region including a representation of a second portion of the subject;
      obtaining a second image of the subject of a second modality, the second image including a third region, the third region including a representation of the first portion of the subject, and the second image lacking a representation of the second portion of the subject;
      obtaining a trained machine learning model; and
      generating, based on the first image and the second image, a synthesized second image using the trained machine learning model, wherein the synthesized second image includes a fourth region and the third region, the fourth region including a representation of the second portion of the subject, and the third region including a representation includes the first portion of the subject.

2. The system of claim 1, wherein the first image includes a positron emission tomography (PET) image, the second image includes a magnetic resonance imaging (MRI) image, and the at least one processor is further configured to cause the system to perform additional operations including:
determining, based on the synthesized second image, attenuation correction data for the first image; and
determining, based on the attenuation correction data, a target PET image of the subject.

3. The system of claim 1, wherein the first image and the second image are acquired by a same imaging device, and the first image and the second image are generated, based on different image reconstruction techniques, using image data acquired by the same imaging device.

4. The system of claim 1, wherein the second image include a truncation artifact causing the second image to lack a representation of the second portion of the subject.

5. The system of claim 1, wherein obtaining a trained machine learning model includes:
obtaining multiple groups of training samples, each group of the multiple groups of training samples corresponding to an object; and
generating the trained machine learning model by training a machine learning model using the multiple groups of training samples in a training process,
wherein for each group of the multiple groups of training samples includes a reference image and a pair of a third image and a fourth image of different modalities, the third image and the fourth image serve as an input of the machine learning model and the reference image serves as a desired output of the machine learning model during the training process, the third image including a complete representation of the object, and the fourth image including a partial representation of the object, and the reference image including a complete representation of the object corresponding to the fourth image.

6. The system of claim 5, wherein obtaining multiple groups of training data includes:
for one of the multiple groups of training samples,
obtaining an initial third image and an initial fourth image of different modalities of an initial object, the initial third image including a complete representation of the initial object, and the initial fourth image including a partial representation of the initial object, the partial representation of the initial object in the initial fourth image missing a representation of a portion of the initial object, the object being at least a portion of the initial object less the missing portion of the initial object; and
determining, based on the initial fourth image, the reference image;
determining, based on the initial third image and the reference image, the third image; and
determining, based on the reference image, the fourth image.

7. The system of claim 6, wherein
determining, based on the initial fourth image, the reference image includes:
determining the reference image by decreasing pixel values of pixels in one or more sections of the initial fourth image, the one or more sections belonging to a first specific region of the initial fourth image that corresponds to the initial object less the missing portion; and
determining, based on the initial third image and the reference image, the third image includes:
generating the third image by decreasing pixel values of pixels in one or more regions of the initial third image corresponding to the one or more sections of the initial fourth image and a second specific region of the initial fourth image that corresponds to the missing portion.

8. The system of claim 6, wherein
determining, based on the initial fourth image, the reference image includes:
designating the initial fourth image as the reference image; and
determining, based on the initial third image and the reference image, the third image includes:
generating the third image by decreasing pixel values of pixels in a specific region of the initial third image that corresponds to the missing portion of the initial object not present in the initial fourth image.

9. The system of claim 6, wherein determining, based on the reference image and the initial fourth image, the fourth image includes:
obtaining a processed reference image by decreasing pixel values of pixels in one or more regions of the reference image; and
designating the processed reference image as the fourth image.

10. The system of claim 6, wherein obtaining multiple groups of training data includes:
for one of the multiple groups of training data,
obtaining an initial third image of a first modality and an initial fourth image of a second modality of an initial object, the initial third image including a complete representation of the initial object, the initial fourth image including a partial representation the initial object, the partial representation of the initial object in the initial fourth image missing a portion of the initial object, the object being at least a portion of the initial object less the missing portion of the initial object;
obtaining a truncated third image by performing a first truncation operation on the initial third image, the truncated third image including a representation of a portion of the initial object;
obtaining a truncated fourth image by performing a second truncation operation on the initial fourth image, the truncated fourth image including a representation of the portion of the initial object present in the truncated third image;
designating the truncated third image and the truncated fourth image as the third image and the reference image, respectively; and
determining the fourth image by performing a third truncation operation on the reference image.

11. The system of claim 6, wherein generating the trained machine learning model by training a machine learning model using the multiple groups of training samples includes:
initializing parameter values of the machine learning model;
for each group of the multiple groups of training samples, training the machine learning model by iteratively updating the parameter values of the machine learning model.

12. The system of claim 1, wherein the trained machine learning model is constructed based on at least one of a convolutional neural network model (CNN), a fully convolutional neural network (FCN) model, or a generative adversarial network (GAN).

13. A method implemented on a computing device having at least one processor and at least one storage device, the method comprising:

obtaining a first image of a subject of a first modality, the first image including a first region and a second region, the first region including a representation of a first portion of the subject, and the second region including a representation of a second portion of the subject;

obtaining a second image of the subject of a second modality, the second image including a third region, the third region including a representation of the first portion of the subject, and the second image lacking a representation of the second portion of the subject;

obtaining a trained machine learning model; and generating, based on the first image and the second image, a synthesized second image using the trained machine learning model, wherein the synthesized second image includes a fourth region and the third region, the fourth region including a representation of the second portion of the subject, and the third region including a representation includes the first portion of the subject.

14. A system, comprising:

at least one storage device storing executable instructions, and at least one processor in communication with the at least one storage device, when executing the executable instructions, causing the system to perform operations including:

obtaining multiple groups of training samples, each group of the multiple groups of training samples corresponding to an object; and generating a trained machine learning model by training a machine learning model using the multiple groups of training samples, wherein for each group of the multiple groups of training samples includes a reference image and a pair of a first image and a second image of different modalities, the first image and the second image serve as an input of the machine learning model and the reference image serves as a desired output of the machine learning model during a training process of the machine learning model, the first image including a complete representation of the object, and the second image including a partial representation of the object, and the reference image including a complete representation of the object corresponding to the second image.

15. The system of claim 14, wherein to obtain multiple groups of training data, the at least one processor is further configured to cause the system to perform additional operations including:

for one of the multiple groups of training data, obtaining an initial first image of a first modality and an initial second image of a second modality of an initial object, the initial first image including a complete representation of the initial object, and the initial second image including a partial representation of the initial object, the partial representation of the initial object in the initial second image missing a portion of the initial object, the object being at least a portion of the initial object less the missing portion of the initial object; and determining, based on the initial second image, the reference image;

determining, based on the initial first image and the reference image, the first image; and determining, based on the reference image, the second image.

16. The system of claim 15, wherein to determine, based on the initial second image, the reference image, the at least one processor is further configured to cause the system to perform additional operations including:

determining the reference image by decreasing pixel values of pixels in one or more sections of the initial second image, the one or more sections belonging to a first specific region of the initial second image that corresponds to the initial object less the missing portion; and to determine, based on the initial first image and the reference image, the first image, the at least one processor is further configured to cause the system to perform additional operations including:

generating the first image by decreasing pixel values of pixels in one or more regions of the initial first image corresponding to the one or more sections of the initial second image and a second specific region of the initial second image that corresponds to the missing portion.

17. The system of claim 15, wherein to determine, based on the reference image, the second image, the at least one processor is further configured to cause the system to perform additional operations including:

obtaining a processed reference image by decreasing pixel values of pixels in one or more regions of the reference image; and designating the processed reference image as the second image.

18. The system of claim 15, wherein to obtain multiple groups of training data, the at least one processor is further configured to cause the system to perform additional operations including:

for one of the multiple groups of training data, obtaining an initial first image of a first modality and an initial second image of a second modality of an initial object, the initial first image including a complete representation of the initial object, the initial second image including a partial representation the initial object, the partial representation of the initial object in the initial second image missing a portion of the initial object, the object being at least a portion of the initial object less the missing portion of the initial object;

obtaining a truncated first image by performing a first truncation operation on the initial first image, the truncated first image including a representation of a portion of the initial object;

obtaining a truncated second image by performing a second truncation operation on the initial second image, the truncated second image including a representation of the portion of the initial object present in the truncated first image;

designating the truncated first image and the truncated second image as the first image and the reference image, respectively; and determining the second image by performing a third truncation operation on the reference image.

19. The system of claim 14, wherein to generate the trained machine learning model by training a machine learning model using the multiple groups of training samples, the at least one processor is further configured to cause the system to perform additional operations including:

initializing parameter values of the machine learning model;

for each group of the multiple groups of training samples, training the machine learning model by iteratively updating the parameter values of the machine learning model.

20. The system of claim 19, wherein iteratively updating the parameter values of the machine learning model includes performing an iterative process, wherein for each iteration of the iterative process, inputting the pair of the third image and the fourth image into the machine learning model;

generating, based on the pair of the third image and the fourth image, an estimated image;

determining a value of a cost function relating to a difference between the estimated image and the reference image; and updating at least some of the parameter values of the machine learning model in response to a determination that a termination condition is unsatisfied.

* * * * *